(12) United States Patent
Lane et al.

(10) Patent No.: US 6,548,055 B1
(45) Date of Patent: *Apr. 15, 2003

(54) IMMUNOLOGIC ENHANCEMENT WITH INTERMITTENT INTERLEUKIN-2 THERAPY

(75) Inventors: H. Clifford Lane, Bethesda, MD (US); Joseph A. Kovacs, Potomac, MD (US); Anthony S. Fauci, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 45 days.

This patent is subject to a terminal disclaimer.

(21) Appl. No.: 09/635,286

(22) Filed: Aug. 9, 2000

Related U.S. Application Data

(63) Continuation of application No. 08/922,218, filed on Sep. 2, 1997, now Pat. No. 6,190,656, which is a continuation of application No. 08/487,075, filed on Jun. 7, 1995, now abandoned, which is a continuation-in-part of application No. 08/452,440, filed as application No. PCT/US94/05397 on May 19, 1994, now Pat. No. 5,696,079, which is a continuation-in-part of application No. 08/063,315, filed on May 19, 1993, now Pat. No. 5,419,900.

(51) Int. Cl.[7] .................. A61K 38/20; A61K 48/00; A01N 43/04; A01N 25/00
(52) U.S. Cl. .................. 424/85.2; 514/44; 514/49; 514/885
(58) Field of Search .................. 424/85.1, 85.2; 514/49, 44, 885

(56) References Cited

U.S. PATENT DOCUMENTS

| | | | |
|---|---|---|---|
| 4,863,730 A | 9/1989 | Karpas | |
| 4,868,157 A | 9/1989 | Durette | |
| 5,026,687 A | 6/1991 | Yarchoan et al. | |
| 5,419,900 A | * 5/1995 | Lane et al. | 424/85.2 |

FOREIGN PATENT DOCUMENTS

| | | |
|---|---|---|
| EP | 343 480 | 11/1983 |
| EP | 426 521 | 5/1991 |
| EP | 452 598 | 10/1991 |

OTHER PUBLICATIONS

Expression of Cloned Genes in Cultured Mammalian Cells, 16.31.*
Anderson et al., Clin. Pharmacokinet., 27(1):19–31 (1994).
Boyd et al., *B Cell Responses to HIV and the Development of Human Monocional Antibodies*, Clin. Exp. Immunol., 88:189–202 (1992).
Cheever et al., *Interleukin 2 Administered In vivo induses the Growth of Cultured T Cells* in vivo, Journal of Immunoogy 132(5):2259–2265 (1984).
Fauser, J. of Cellular Biochemistry 45:353–358 (1991).
Karwowska et al., *Passive Immunization for the Treatment and Prevention of HIV Infection*, Biotechnology Therapeutics 2(1–2):34–48 (1991.
Kohler et al., *Enhanced in vivo Generation of LAK Cells by Repetitive Administration of IL–2, a Phase I Clinical Study*, Immunology and Cytokines, Proc. Of ASCO 6:980 (1987).
Kovacs et al., Prog. and Abstr. Interscience Conf. on Antimicrobial Agents and Chemotherapy 33:328 (1993).
Lane et al., J. Biol. Response Mos. 3:512–516 (1984).
Lane et al., AIDS Research Human Retroviruses 10(Suppl. 3):S155 (1994).
Matory et al., Journal of Biological Response Modifiers 4:377–390 (1985).
Oyaizu et al, PNAS 87:2379–2383 (1990).
Reddy et al., *Differential Effects of Interferon–$\alpha 2$ and Interleukin–2 on Natural Killer Cell Activity in Patients with Acquired Immune Deficiency Syndrome*, J. of Biol. Response Modifiers pp. 379–386 (1984).
Roberts et al., *Targeting of Human Immunodeficiency Virus–Infected Cells by $CD8^+T$ Lymphocytes Armed With Universal T–Cell Receptors*, Blood 84(9):2878–2889 (1994).
Schwartz et al., Biotherapy 2:119–136 (1990).
Schwartz et al., *Safety and Effects of Interleukin–2 Plus Zidovudine in Asymptomatic Individuals Infected with Human Immunodeficiency Virus*, J. Acquir. Immune Defic. Syndr., 4(1):11–23 (1991).
Sneller et al., Annals New York Academy of Sciences 685:687–696 (1993).
Stein et al., J. Infect. Dis. 165:352–363 (1993).
Teppler et al., *Interleukin–2 in HIV Infection: Safety and Systemic Effect of Low Dose Intradermal Administration*, Clin. Res. 39:314A (1991).

(List continued on next page.)

*Primary Examiner*—Remy Yucel
*Assistant Examiner*—Celine Qian
(74) *Attorney, Agent, or Firm*—Klarquist Sparkman, LLP

(57) ABSTRACT

A method for activating a mammalian immune system entails a series of IL-2 administrations that are effected intermittently over an extended period. Each administration of IL-2 is sufficient to allow spontaneous DNA synthesis in peripheral blood or lymph node cells of the patient to increase and peak, and each subsequent administration follows the preceding administration in the series by a period of time that is sufficient to allow IL-2 receptor expression in peripheral or lymph node blood of the patient to increase, peak and then decrease to 50% of peak value. This intermittent IL-2 therapy can be combined with another therapy which targets a specific disease state, such as an antiretroviral therapy comprising, for example, the administration of AZT, ddI or interferon alpha. In addition, IL-2 administration can be employed to facilitate in situ transduction of T cells in the context of gene therapy. By this approach the cells are first activated in vivo via the aforementioned IL-2 therapy, and transduction then is effected by delivering a genetically engineered retroviral vector directly to the patient.

11 Claims, 28 Drawing Sheets

OTHER PUBLICATIONS

Teppler et al., *Efficacy of Low Doses of the Polyethylene Glycol Derivative of Interleukin–2 in Modulating the Immune Response of Patients with Human Immunodeficiency Virus Type 1 Infection*, J. Infect. Dis. 167:291–298 (1993).

Teppler et al., J. Exp. Med. 177:483–492 (1993).

West, *Lumphokine–Activated Killer Lumphocytes: Biotherapeutic Clinical Trials*, Imm. Ser. 48:79–92 (1989).

Wood et al., *Safety and Efficacy of Polyethylene Glycol–Modified Interleukin–2 and Zidovudine in Human Immunodeficiency Virus Type 1 Infection: A Phase I/II Study*, J. Infect. Dis. pp. 519–524 (1993).

Geszyme Catalog, Cytokine Research Products pp. 19–20 (1991).

J. National Cancer Institute 85(8):622–632 (1993).

\* cited by examiner

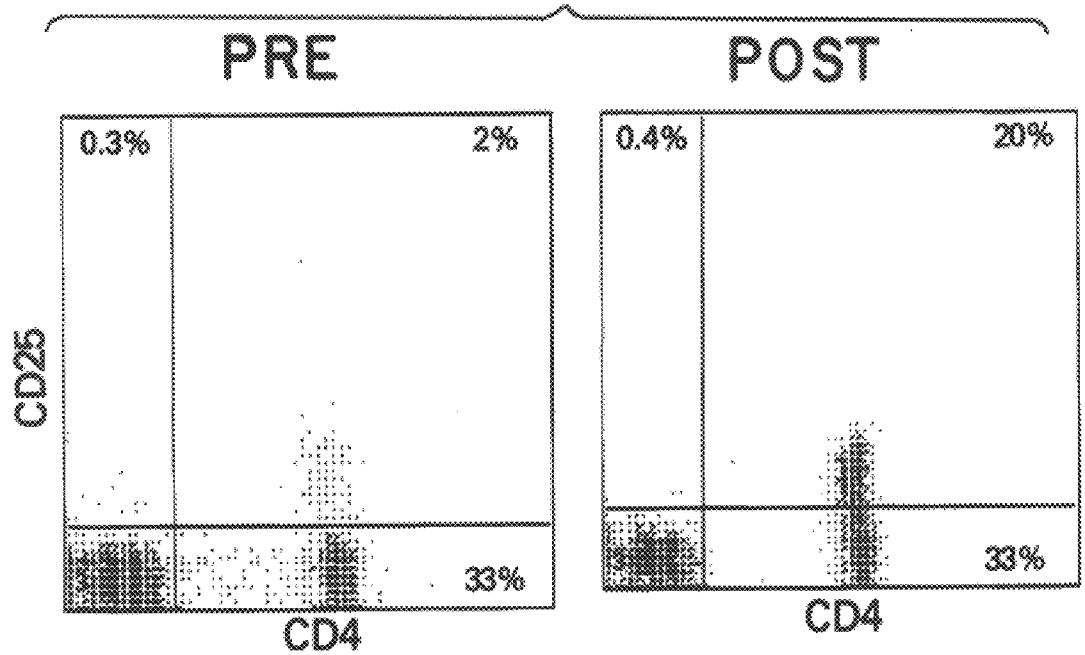
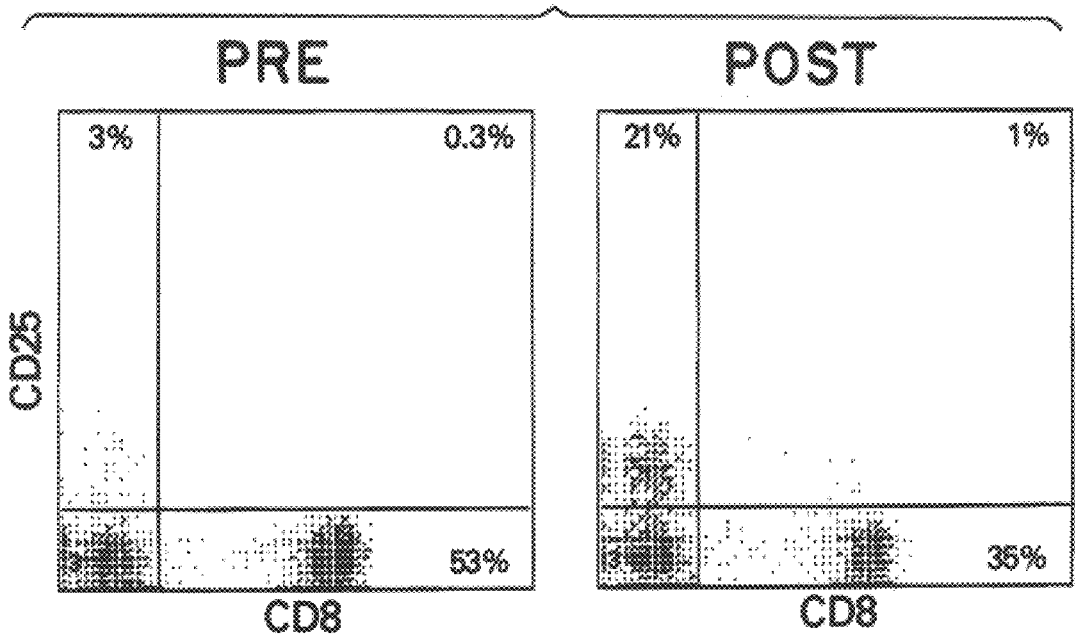

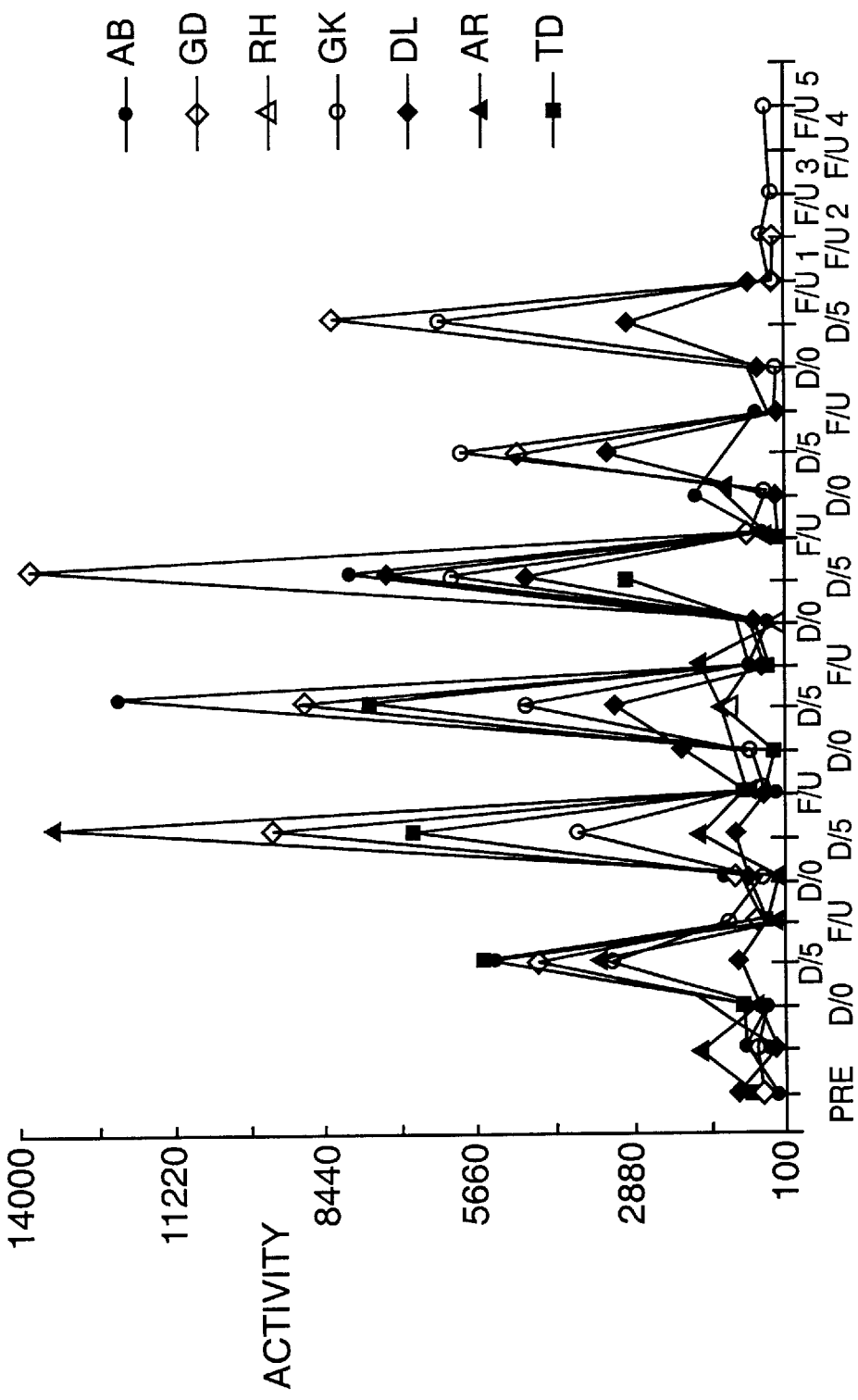

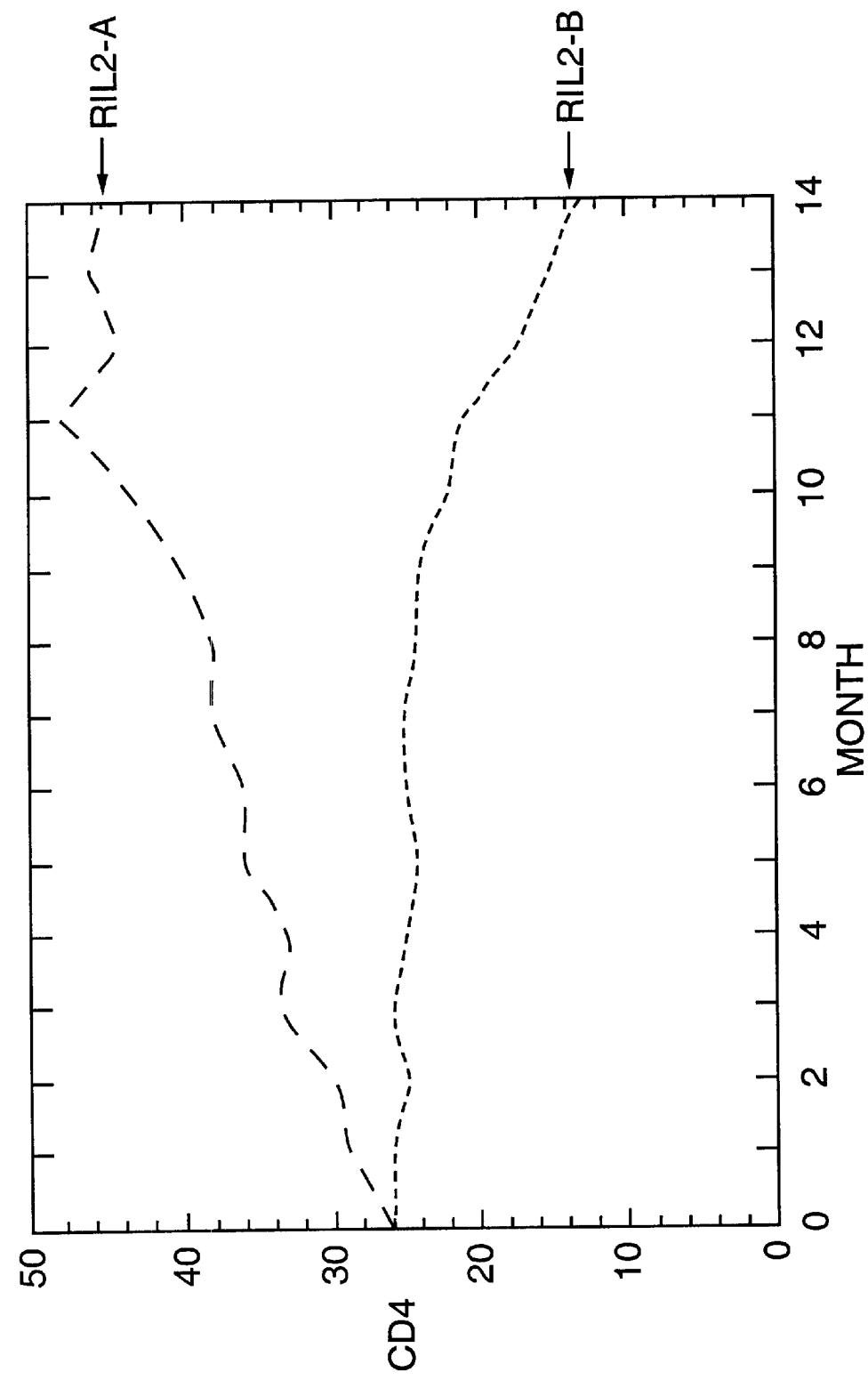

IMMUNOLOGIC ENHANCEMENT WITH INTERMITTENT INTERLEUKIN-2 THERAPY

This application is a continuation of U.S. patent application Ser. No. 08/922,218, filed Sep. 2, 1997, now issued as U.S. Pat. No. 6,190,656 which is a continuation of U.S. patent application Ser. No. 08/487,075, filed on Jun. 7, 1995, now abandoned, which is a continuation-in-part of U.S. application Ser. No. 08/452,440, filed May 26, 1995, now issued as U.S. Patent No. 5,696,079, which is a § 371 of PCT Application No. PCT US94/05397, filed May 19, 1994, which is a continuation-in-part of U.S. application Ser. No. 08/063,315, filed May 19, 1993, now issued as U.S. Pat. No. 5,419,900.

This application claims the benefits of priority under 35 USC § 120 of U.S. application Ser. No. 08/063,315, filed May 19, 1993, the contents of which are incorporated by reference.

Work relating to this invention was supported in part with federal funds under contract number NO1-AI-05058 from the National Institute of Allergy and Infectious Disease (NIAID), National Institutes of Health.

FIELD OF THE INVENTION

The present invention pertains to a method for activating the immune system of a patient by intermittently administering interleukin-2 (IL-2) to that patient. Such administration of IL-2 can optionally be combined with other therapies, such as anti-retroviral, anti-bacterial or anti-fungal therapies, suitable for treatment of the patient's condition. This invention also relates to an approach to gene therapy that entails administering IL-2 to a patient so as to facilitate in situ lymphocyte transduction by a retroviral vector also administered to the patient.

BACKTGROUND OF THE INVENTION

Attempts at immune activation and restoration in the past have utilized bone marrow transplantation or lymphocyte transfers (H. C. Lane et al., *Ann. Internal Med.* 113: 512–19 (1990)), immunomodulating agents such as immuthiol (J. M. Lang et al., *Lancet* 24: 702–06 (1988)) or isoprinosine (C. Pedersen et al., *N. Engl. J. Med.* 322: 1757–63 (1990)), and recombinant cytokines such as interferon alpha (IFN-α) and IL-2. H. C. Lane et al., *Ann. Intern. Med.* 112: 805–11 (1990); H. C. Lane et al., *J. Biol. Response Mod.* 3, 512–16 (1984); D. H. Schwartz et al., *J. Acquir. Immune Defic. Syndr.* 4, 11–23 (1991); P. Mazza et al., *Eur. J. Haematol.* 49: 1–6 (1992); H. W. Murray et al., *Am. J. Med.* 93: 234 (1992); H. Teppler et al., *J. Infect. Dis.* 167: 291–98 (1993); P. Volberding et al., *AIDS Res. Hum. Retroviruses* 3: 115–24 (1987). These studies have resulted in minimal or only transient immune system restoration.

The use of biologic response modifiers in general, and of IL-2 in particular, is an active area of clinical research. Interleukin-2 is a T cell-derived lymphokine with a number of immunomodulating effects including activation, as well as induction of proliferation and differentiation, of both T and B lymphocytes. K. A. Smith, *Science* 140: 1169–76 (1988). Exogenous IL-2 has been shown in vitro to increase the depressed natural killer cell activity and cytomegalovirus-specific cytotoxicity of peripheral blood mononuclear cells from patients with AIDS, as well as to increase IFN-γ production by lymphocytes from patients with AIDS. A. H. Rook et al., *J. Clin. Invest.* 72: 398–403 (1983); H. W. Murray et al., *loc. cit.* 76: 1959–64 (1985).

IL-2 given by high dose infusion has been employed in the treatment of renal cell carcinoma and melanoma. *J. Nat'l Cancer Inst.* 85(8): 622–32 (1993). For example, doses of 36 million international units (MU) given continuously over a period of 24 hours has been used in the treatment of cancer (18 MU is equivalent to about 1 mg protein). *Lancet* 340: 241 (1992). The use of high doses of IL-2 generally is not well tolerated by patients, however, and side effects are more pronounced at such high levels.

Subcutaneous administration of IL-2 has been evaluated extensively in patients with metastatic cancer, although most often in conjunction with alpha interferon. Our current data suggest that the maximum tolerated dose of subcutaneous IL-2 given over a five day course of therapy is about 21 MU/day. Most previous trials used a four week regimen of dosing. The highest subcutaneous dose of IL-2 delivered in a single agent setting was delivered in an intrapatient dose escalation trial where four patients tolerated doses equal to or in excess of 24 MU/m2/day. These patients had already received more than one month of IL-2, so these doses were tolerable in spite of chronic dosing. Whitehead et al., *Cancer Res* 50: 6708 (1990). A similar trial delivered doses in the range of 18 MU/patient on a five day basis followed by lower doses for prolonged periods. Sleijfer et al., *J. Clin. Oncol.* 10:1119 (1992); Lissoni et al., *Eur. J. Cancer* 28: 92 (1992). Other trials have used lower dose IL-2 regimens with similar toxicities. Urba et al., *Cancer Res.* 50: 185 (1990); Stein et al., *Br. J. Cancer* 63: 275 (1991); Atzpodien et al., *Mol. Biother.* 2: 18 (1990). Thus, subcutaneous dose levels of IL-2 in the range of 18–24 MU/day have been reasonably well tolerated over one month of therapy.

Subcutaneous IL-2 is poorly absorbed, however, and local reactions can be dose-limiting. McElrath et al., *Proc. Nat'l Acad. Sci., USA* 87: 5783 (1990), suggest that locally high concentrations of IL-2 can have systemic effects as assessed by activation of lymphocytes remote from the site of injection. Further, in HIV seronegative populations, subcutaneous IL-2 at tolerable doses has led to increases in lymphocyte counts and improved cytotoxicity as assessed by NK and LAK activity. Most of the patients treated with these regimens had metastatic cancer and the additional observation of objective tumor responses suggests that the immune activation was clinically important.

Other researchers are evaluating IL-2 in the treatment of other diseases, including HIV infection. The use of lower doses of IL-2 in a continuous therapy regime has been disclosed by Yarchoan et al., U.S. Pat. No. 5,026,687. More specifically, Yarchoan et al. teach the use of the anti-retroviral agent ddI in combination with IL-2 administered continuously at a dosage between 25,000 to 1 million international units (MU) per day, for a period of three months. While Yarchoan et al. predict that "beneficial results" will accompany the combined ddI/IL-2 regimen, they do not attribute these results to IL-2 per se. Moreover, dosages at this lower level have been shown to cause an initial increase in CD4 level that was transient in nature: that is, CD4 levels returned to baseline within 6 months after the completion of the treatment.

Many researchers feel that the use of IL-2 is contraindicated in patients with HIV infection due to its potential to activate HIV. No method of treatment of HIV with IL-2 has been disclosed which results in a sustained response or which yields long-term beneficial results.

Cells that have been stimulated to actively synthesize DNA are susceptible to transduction by gene transfer therapy. Present methods of gene therapy require a complicated, in vitro transformation. More specifically, cells are removed from a patient, activated in vitro, and used to establish cell lines which are then gene-transduced in vitro and re-implanted in the patient. This procedure is expensive, and its success its limited due to the potential of failure at each of the steps of activating the cells, effecting the transduction, and implanting the cells in the patient for expression.

Attempts at using retroviral vectors to effect in vivo gene transfer have been limited. Retroviruses will only integrate stably into target cells that are actively synthesizing DNA. This integration must occur before retroviral gene expression can be effected. Because only a fraction of cells are actively producing DNA at any giving time, such in vivo gene transfer methods have shown little success.

SUMMARY OF THE INVENTION

It is therefore an object of the present invention to provide a means for activating and expanding the elements of the immune system that employs IL-2 but that avoids the pronounced side-effects associated with conventional IL-2 treatments.

It is also an object of the present invention to provide a means for treating a wide variety of disease states, including HIV infection, through the use of IL-2 therapy.

It is a further object of the present invention to provide an approach to effecting retroviral vector-mediated transduction in situ, in the context of gene therapy, for a patient whose immune system has been activated by the administration of IL-2.

In accomplishing these and other objects, there is provided, in accordance with one aspect of the present invention, a method for treating a disease state characterized by an immunological impairment, by the intermittent administration of IL-2 wherein IL-2 is administered to the patient in an amount that is sufficient to increase the CD4 count in the patient. In accordance with this method, the IL-2 is administered in a series of administrations effected intermittently, each administration being continuous over a period of time that is sufficient to allow spontaneous DNA synthesis in the patient to increase and peak, and each subsequent administration following the preceding administration in the series by a period of time that is sufficient to allow IL-2 receptor expression in the patient to increase, peak and then decrease to 50% of peak value.

In another aspect of the present invention, the period of time that each subsequent administration follows the preceding administration is sufficient for CD4 counts to increase and then decrease to about 125% of a baseline value.

In accordance with one aspect of the present invention, the IL-2 administration is effected by intermittent continuous infusions, and in accordance with another aspect of the present invention, the administration is effected by an intermittent series of subcutaneous injections, which may be given in one or more injections per day.

In accordance with another aspect of the present invention, a compound (or compounds) which blocks the activity of pro-inflammatory cytokines is administered concomitantly with the IL-2 therapy to minimize the side effects of the IL-2.

In accordance with another aspect of the present invention, the IL-2 therapy is combined with another therapy, such as anti-retroviral therapy, which targets a specific disease state.

Another aspect of the present invention provides a kit for activating the immune system of a patient comprising (i) a liquid preparation comprising an amount of IL-2 in a pharmaceutically acceptable carrier and (ii) instructions on administering the preparation to a patient suffering from an immunological impairment or infectious disease in a series of administrations effected intermittently, such that (A) each administration is continuous over a period of time that is sufficient to allow spontaneous DNA synthesis in the patient to increase and peak, and (B) each subsequent administration follows the preceding administration in the series by a period of time that is sufficient to allow IL-2 receptor expression in the patient to increase, peak and then decrease to 50% of peak value.

Another aspect of the present invention provides a process for modulating the immune system of a patient, comprising the steps of: (A) activating the immune system by the procedure described above, and (B) administering a retroviral vector to the patient to effect in situ transformation of lymphocytes.

Additional objects and advantages of the invention will be set forth in part in the description that follows, and in part will be obvious from the description, or may be learned by practice of the invention. The objects and advantages may be realized and obtained by means of the uses and compositions particularly pointed out in the appended claims.

BRIEF DESCRIPTION OF THE DRAWINGS

FIGS. 2B–2G show a two-color fluorescent activated cell sorter (FACS) analysis of IL-2 receptor and HLA-DR expression determined on frozen cells of patient 2 obtained prior to IL-2 therapy, and at week 48 (five weeks after the fifth course of IL-2).

FIG. 4 shows levels of DNA synthesis occurring in vivo in patients receiving a 5-day continuous infusion of IL-2.

FIG. 5 shows changes in CD4 count for patients receiving anti-retroviral therapy alone (Group B) or receiving anti-retroviral therapy and intermittent IL-2 therapy according to the present invention (Group A).

DETAILED DESCRIPTION OF THE PREFERRED EMBODIMENTS

Figure 1A:
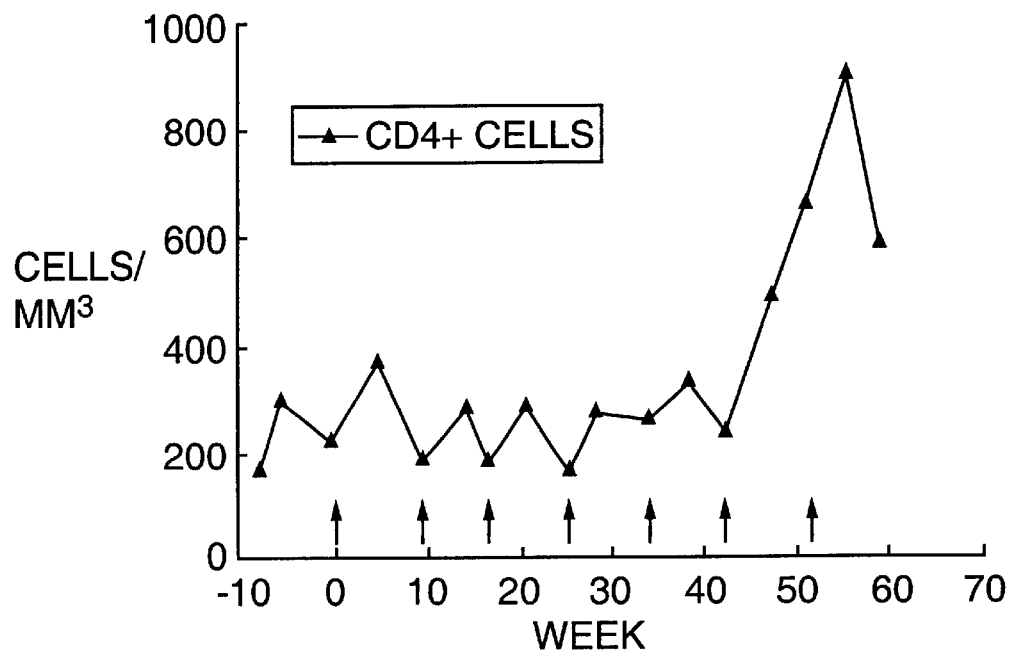
FIGS. 1A–1D show changes in CD4 cell count and blastogenic responses to tetanus toxoid and pokeweed mitogen (PWM) for patients 1 and 3 during a year of intermittent IL-2 therapy.

The present invention provides a method for increasing the level of immune function of patients, including immunodeficient patients, by administering IL-2. The increase in immune function typically manifests itself as an increase in helper/inducer T-cell function. More particularly, the increased immune function can include, for example, an increase in CD4 count, a restoration of lymphocyte function, an increase in the expression of IL-2 receptors (IL-2r), and/or an increase in T-cell responsiveness.

The methods of the present invention can be effective against disease states in which IL-2 plays a role in the associated immune response. The targeted disease state can comprise, for instance, an infection of the patient by a pathogen against which a cellular immune response is the principal mechanism for specific immunity therefor in the patient, such as viral infections. See Abbas et al., CELLULAR AND MOLECULAR IMMUNOLOGY 309–10 (W. B. Saunders Co., Philadelphia 1991). Illustrative of specific disease states in treatment of which the present invention can be applied are HIV infection and other diseases characterized by a decrease of T-cell immunity, for example, mycobacterial infections like tuberculosis and fungal infections such as cryptococcal disease. This method also can be used in the treatment of secondary infections that occur in patients with suppressed immune systems, such as the opportunistic infections that occur in AIDS patients.

While prior attempts at the therapeutic use of IL-2 in treating AIDS patients have been largely unsuccessful, the therapeutic use of IL-2 according to the present invention elicits maximal T-cell activation and T-cell expansion inpatients with HIV infection, and should be effective in a qualitatively similar manner in any patient. The method promotes at least partial restoration of immune function of HIV-infected patients, as demonstrated by sustained improvements in CD4 counts and by restoration of T-cell responsiveness to recall antigens and mitogens, with results sustained up to twenty-two months after IL-2 infusion has been stopped. CD4 levels have been restored to and sustained at levels seen in healthy patients (800–1200 cells/$mm^3$)or even higher, indicating a restoration of the immune system as a result of the IL-2 therapy.

The present invention utilizes a series of administrations of IL-2 effected intermittently. An optimal duration of each administration and optimal time period between administrations has not been determined, and probably will vary from patient to patient. One skilled in the art would be able to modify a protocol within the present invention, in accordance with conventional clinical practice, to obtain optimal results for a given patient. For example, the relationships between IL-2 administration, T cell activation, T cell proliferation and T cell expansion and IL-2 receptor expression in vivo can be used to develop more optimal regimens of IL-2 administration.

Applicants' studies have revealed that during each course of IL-2 administration, spontaneous DNA synthesis in peripheral blood or lymph node cells (a measure of T cell proliferation) increases, peaks and decreases. In one preferred embodiment of the present invention, this spontaneous DNA synthesis is measured to determine the optimal duration of each IL-2 administration, and IL-2 is administered until the level of spontaneous DNA synthesis has increased and peaked.

By "spontaneous DNA synthesis" is meant DNA synthesis that is not induced by any in vitro means. One method of determining spontaneous DNA synthesis is to examine spontaneous blast transformation, for example, by counting the fraction of cells, such as helper or killer T-cells, that are dividing. In this method, peripheral blood or lymph node cells is obtained from patients, and the fraction of cells that are dividing are counted. This can be accomplished by measuring the rate of new DNA synthesis or analyzing the DNA content of cells. IL-2 is administered until this measurement reaches a peak value.

In general, IL-2 will be administered for a period of time ranging from 1 day to about 2 weeks. It is believed that administration periods of less than one day will not be effective, and administration periods of longer than 2 weeks will not show an advantage over shorter periods. Studies have shown that peak activation of the immune system usually occurs at about the 5th day of IL-2 administration.

The optimal interval between administrations can be determined by measuring other parameters. For example, experimental data show that the level of soluble IL-2 receptor expression increases during IL-2 administration and then decreases. The level of soluble IL-2 receptor expression is believed to be an indicator of when the patient's immune system has passed through a "refractory period" (following an IL-2 administration) and is capable of responding to another administration. In a preferred embodiment of the present invention, therefore, each subsequent administration of IL-2 follows the preceding administration in the series by a period of time that is sufficient to allow soluble IL-2 receptor expression in the patient to increase, peak and then decrease to 50% of peak value or less.

Figure 19:
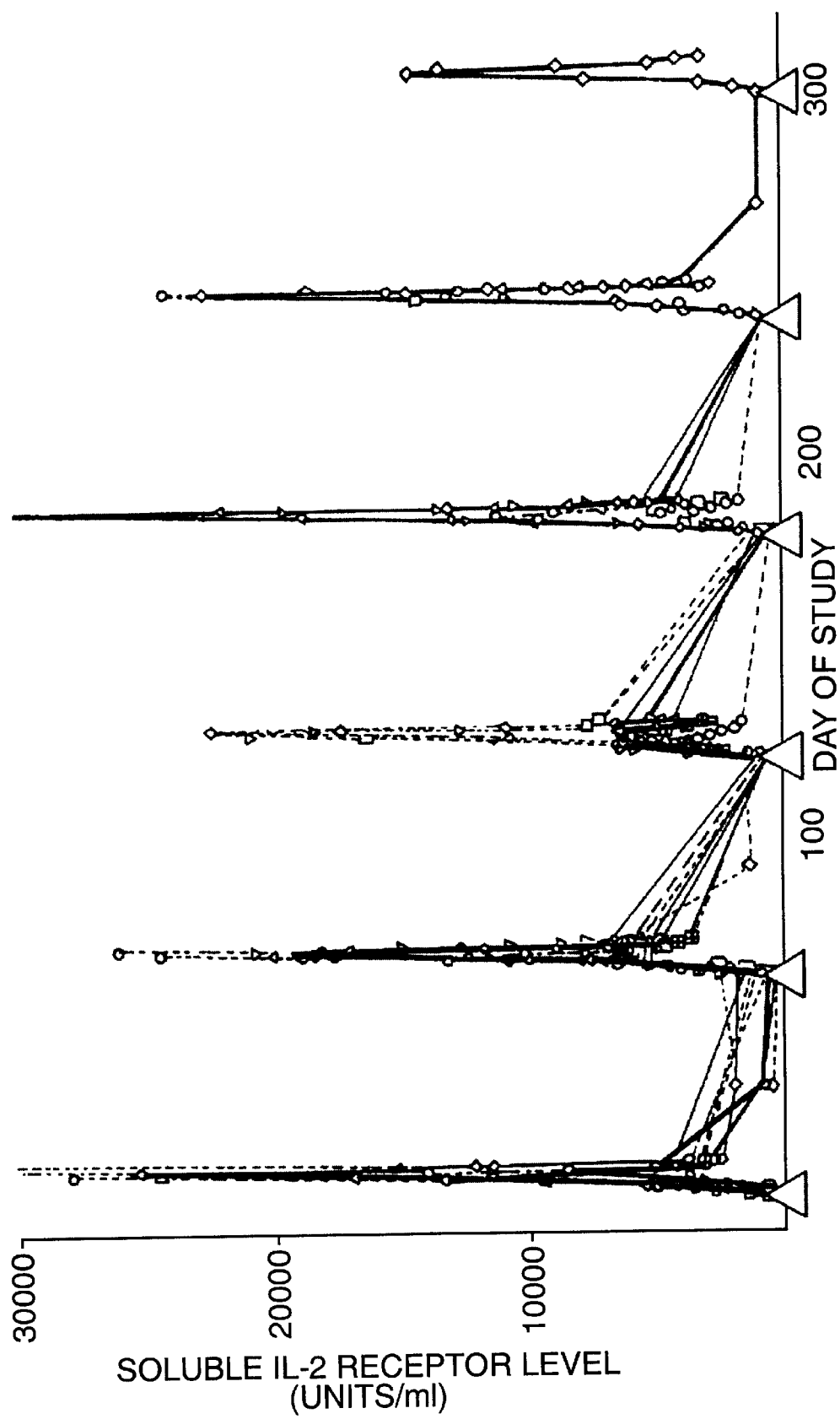
FIG. 19 shows changes in levels of soluble IL-2 receptors during intermittent IL-2 therapy.

To monitor soluble IL-2 receptor level, peripheral blood or lymph node cells are obtained from patients and examined, for example, by performing an appropriate ELISA or by flow cytometry which is keyed to a dye that binds IL-2 receptor. The information thus obtained is used to determine the optimal timing of successive administrations. Illustrative of such data are those results depicted in FIG. 19. By another, roughly comparable measure, the inter-administration interval can be the time needed for the levels of soluble IL-2 receptors to return to, for example, under about 1000 units/ml.

Changes in CD4 count also may be used to determine optimal intervals. During the intermittent IL-2 therapy of the present invention, CD4 counts increase during times of IL-2 administration. While CD4 counts generally remain well above initial, pre-therapy levels, they gradually decrease to some extent over time. These changes in CD4 count can be monitored to select an optimal interval between administrations. For example, the interval can be chosen to correspond to the time it takes for the CD4 count to return to about 125% of a pre-administration baseline value.

Time periods between administrations may range, for example, from 4 weeks to 6 months, or even one year. It is believed that administrations closer than 4 weeks apart may be too close to yield the benefits of intermittent therapy, although in some patients close administrations may be effective. In light of the side effects associated with IL-2 therapy, however, longer time periods between infusions are preferred. For example, the IL-2 can be administered every 6 weeks, 8 weeks, 12 weeks or six months, and beneficial results may be seen. It is hoped that treatments as far apart as one year or longer will show sustained beneficial results.

The intermittent IL-2 therapy of this invention can constitute a lifelong treatment regime, with the cycles of IL-2 infusions continuing indefinitely. It is believed that, once a patient's immune system has been restored by this method (as evidenced, for example, by sustained CD4 counts), subsequent infusions can be administered further and further apart. For example, a patient initially receiving infusions every 8 weeks may subsequently receive infusions every 6 months, and then once a year, and still maintain elevated CD4 counts.

In one ongoing study, patients are continuously infused with IL-2 at the dosages described below for 5 days, no IL-2 is given for 8 weeks, and IL-2 is again given continuously for 5 days. The cycle has continued, and patients have undergone up to 19 courses of IL-2.

The dosages of IL-2 which are characteristic of the present invention range from 1 million international units (MU)/day to 24 MU/day. These doses are much lower than doses currently licensed for use in the treatment of cancer. In one embodiment, IL-2 is administered by continuous IV infusion over 5 days, once every 8 weeks, at doses between about 6 to 18 million international units (MU)/day. Patients have been observed to show initial increases in expression of IL-2 receptors after a single course of this therapy. Although a dosage of 18 MU/day is preferred, some patients may not be able to tolerate this high level of IL-2, and dosages of 6–12 MU/day may be used with benefit.

As set forth above, the IL-2 may be administered by continuous infusion. The infusion may be through a central line, i.e., through the neck, or peripherally, for example, through the arm. Advantageously, the continuous IL-2 infusion can be administered peripherally. By contrast, previously disclosed, low-dose, continuous IL-2 treatments require central line infusions, which cause more discomfort to the patient.

Alternatively, the IL-2 is administered by subcutaneous injection. That is, an intermittent course of IL-2 is followed wherein IL-2 is given by subcutaneous injection at a daily dose of from 1 to 24 million international units (MU)/day for a period of several days, followed by a period of one or more weeks when no IL-2 is administered, and then a period when IL-2 is again given by subcutaneous injection. The above-described daily dose may be effected by one or more injections. For example, 3–15 MU/day may be divided into 1–3 doses per day, and given for 3–8 days.

By IL-2 is meant any form of IL-2 that has a biological activity that is similar to native human IL-2. IL-2 can be produced by a prokaryotic microorganism or an eukaryotic cell that has been transformed with a native or modified human IL-2 DNA sequence. IL-2 has hydrophobic and hydrophilic regions, and is unglycosylated when produced in *E. coli*. Synthetic IL-2 with amino acid sequences which differ from the native sequence as a result of alterations (deletions, additions, substitutions) that do not cause an adverse functional dissimilarity between the synthetic protein and native human interleukin-2 can be used in accordance with the present invention. For examples of such proteins see U.S. Pat. No. 4,738,927, EP 0 091 539, and EP 0 088 195, and the recombinant IL-2 muteins described in EP 0 109 748 and U.S. Pat. No. 4,518,584. The respective contents of these patents and patent applications are hereby incorporated by reference.

The precise chemical structure of IL-2 depends on a number of factors. As ionizable amino and carboxyl groups are present in the molecule, a particular protein may be obtained as a acidic or basic salt, or in neutral form. All such preparations which retain their activity when placed in suitable environmental conditions are included in the definition of IL-2 herein. Further, the primary amino acid sequence of the IL-2 protein may be augmented by derivitization using sugar moieties (glycosylation) or by other supplementary molecules such as lipids, phosphate, acetyl groups and the like. It may also be augmented by conjugation with saccharides. Certain aspects of such augmentation are accomplished through post-transnational processing systems of the producing host; other such modifications may be introduced in vitro. In any event, such modifications are included in the definition of IL-2 herein so long as the activity of the IL-2 protein is not destroyed. It is expected that such modifications may quantitatively or qualitatively affect the activity, either by enhancing or diminishing the activity of the protein. Further, individual amino acid residues in the chain may be modified by oxidation, reduction, or derivatization, and the protein may be cleaved to obtain fragments which retain activity. Such alterations which do not destroy activity do not remove the protein sequence from the definition of IL-2 herein.

Finally, modifications to the primary structure itself, by deletion, addition, or alteration of the amino acids incorporated into the sequence during translation, can be made without destroying the activity of the protein. For example, at least one cysteine residue which is not essential to biological activity, present in the biologically active protein, and free to form a disulfide link, may be deleted or replaced with a conservative amino acid to eliminate sites for intermolecular crosslinking or incorrect intramolecular disulfide bond formation. Such modified proteins, known as "muteins," are described in U.S. Pat. Nos. 4,518,584, and 4,752,585, the respective contents of which are hereby incorporated by reference.

A conservative amino acid alteration in this context is defined as one which does not adversely affect biological activity and involves substitutions or deletion of the cysteine at position 125 or at position 104 (numbered in accordance with the native molecule). The preferred conservative amino acids that are useful to replace cysteine are: serine, alanine, threonine, glycine, valine, leucine, isoleucine, tyrosine, phenylalanine, histidine, and tryptophan. The preferred conservative amino acids that are useful to replace methionine are the same as for cysteine with the addition of aspariginine and glutamine, but exclude histidine and tryptophan.

A preferred IL-2 mutein has the cysteine at position 125 replaced with a serine residue and/or the methionine at amino acid position 104 replaced with an alanine residue. Other preferred IL-2 muteins include those which have as many as six N-terminal deletions. For example, des-ala1 des-pro2 des-thr3 des-ser4 des-ser5 des-ser6 IL-2 is an N-minus six muteins, other muteins may have fewer amino acid deletions. Specifically preferred muteins are, for example, des-ala1 des-pro2, des-thr3, des-ser4 ala104 ser125 IL-2, and des ala, ser125 IL-2.

As set forth above, recombinant IL-2 can be produced by a prokaryotic microorganism or by eukaryotic cells. Preferably, the IL-2 is produced by transforming a prokaryotic microorganism with DNA to produce a protein that possesses native human IL-2 activity. Examples of transformed microorganisms are described in the European applications and U.S. patents discussed above. Bacteria are preferred prokaryotic microorganisms for producing IL-2 and *E. coli* is especially preferred. A typical transformed microorganism useful in the present invention is *E. coli* K-12, strain MM294, transformed with plasmid pLW1 (deposited with the American Type Culture Collection on Aug. 4, 1983, by Cetus Corporation under the provisions of the Budapest Treaty and assigned Accession No. 39,405). Synthetic recombinant IL-2 also can be made in eukaryotes, such as yeast or human cells.

Processes for growing, harvesting, disrupting, or extracting the IL-2 from cells are substantially described in U.S. Pat. Nos. 4,604,377, 4,738,927, 4,656,132, 4,569,790, 4,748,234, 4,530,787, 4,572,298, 5,248,769, and 5,162,507, the respective contents of which are hereby incorporated by reference. Other procedures for purifying native IL-2 from T-cells are described by Watson et al., *J. Exp. Med.* 150: 849–861 (1979); Gillis et al., *J. Immunology* 124: 1954–62 (1980); Mochizuki et al., *J. Immun. Meth.* 39: 185–201 (1980); Welte et al., *J. Exp. Med.* 156: 454–464 (1982); EP 0 092 163 and EP 0 094 317, the respective contents of which are incorporated by reference.

After the IL-2 is produced and purified it is incorporated into a pharmaceutical composition. This composition may contain other compounds that increase the effectiveness or promote the desirable qualities of IL-2. The composition must be safe for administration via the route that is chosen, it must be sterile, retain bioactivity, and it must stably solubilize the IL-2. To maintain the sterility and to increase the stability of IL-2, the composition is lyophilized and reconstituted prior to use.

Formulations that are useful in the present method are shown in various patents and publications. For example, U.S. Pat. No. 4,604,377 shows a formulation which has a therapeutic amount of IL-2, which is substantially free from non-IL-2 protein and endotoxin, a physiologically acceptable water soluble carrier, and a sufficient amount of a surface active agent to solubilize the IL-2, such as sodium dodecyl sulfate. Other ingredients can be included, such as sugars. U.S. Pat. No. 4,766,106 shows formulations including polyethylene glycol (PEG) modified IL-2. Wood et al., *J. Infect. Dis.* 167: 519–25 (1993) and Teppler et al., *J. Infect. Dis.* 167: 291–8 (1993) discuss the use of PEG-IL-2 to treat HIV infection. U.S. Pat. No. 5,037,644 shows IL-2 formulated with various non-ionic surfactants selected from the group consisting of polyoxyethylene sorbitan fatty acid esters (Tween-80), polyethylene glycol monostearate, and octylphenoxy polyethoxy ethanol compounds (Triton X405). U.S. Pat. No. 4,992,271 discloses IL-2 formulations comprising human serum albumin and U.S. Pat. No. 5,078,997 discloses IL-2 formulations comprising human serum albumin and amino acids. All respective contents of the above patents and publications are hereby incorporated by reference.

Polymer-modified IL-2 or the unmodified IL-2 can be formulated for parenteral administration. For example, see U.S. Pat. No. 4,992,271, wherein IL-2 is formulated at physiological pH using serum albumin; U.S. Pat. No. 4,816,440, wherein IL-2 is formulated with sodium laureate; U.S. Pat. No. 4,605,377, wherein IL-2 is formulated with water soluble carrier such as mannitol and sodium dodecyl sulfate; U.S. Pat. No. 4,894,226, wherein IL-2 is connected to a flexible spacer and a polyproline molecule; U.S. Pat. No. 5,037,644, wherein IL-2 is formulated with various nonionic surfactants; U.S. Pat. No. 5,102,872, wherein polymer modified IL-2 is formulated in a controlled release formulation, including a polylactide co-glycoside polymer and human serum albumin; and U.S. Ser. No. 373,928, which discloses IL-2 in combination with a cyclodextrin. The respective contents of these patents and patent applications are hereby incorporated by reference.

Various compounds can be added as stabilizers for IL-2. A "stabilizer" is defined as an amino acid, vitamin, polymer, fatty acid, or a salt of a low molecular weight organic acid which will cause IL-2 to remain stably soluble in an aqueous solution or after lyophilization and reconstitution. Some of these stabilizers exist in the body and many have a history of being injected into humans. Thus, they may be considered relatively safe because they do not present the same toxicity problems as do other formulants.

Preferred amino acids are the levo rotatory (L) forms of carnitine, arginine, and betaine, more preferred amino acid stabilizers are arginine, or a mixture of arginine and carnitine, the most preferred amino acid stabilizer is a mixture of canitine and arginine. A preferred vitamin is pyrodixin (B6), preferably as a hydrochloride salt, either alone or in combination with the amino acids. A preferred polymer is polyvinylpyrrolidone (PVP) with an average molecular weight of between 2,000 and 3,000, more preferably about 2,500; or polyethylene glycol (PEG) with an average molecular weight between 3,000 and 5,000, more preferably about 4,000. Polymers outside of these ranges do not work as satisfactorily. A preferred fatty acid is capric acid and a preferred salt of a low molecular weight organic acid is succinic acid. More preferably these acids are sodium salts.

The pH of the combination is preferably adjusted to between 5.0 and 8.5 before adding the IL-2, more preferably between 6.0 and 8.0, most preferably between 6.0 and 7.5. When carnitine is used singly to stabilize IL-2, the solution pH will be approximately 3 to 3.5. Consequently, it is preferred to include an additional factor such as serum albumin. The serum albumin may be derived from humans, pigs, cows, and the like. Similarly, when arginine is used alone to stabilize IL-2 the solution pH may between 9.5 to 10.5. A mixture of arginine and serum albumin (before IL-2 addition) within the pH range of 6 to 8.5 would give a pharmaceutically acceptable formulation. When both arginine and canitine are used as the stabilizer, it is preferred to mix them together to bring the pH into a range between 5.0 and 8.5, more preferably between 6.0 and 8.0, most preferably between 6.0 and 7.5 before adding the IL-2. This combination is most preferred.

Typically, the stabilizer concentration is between 0.1 and 10 w/v %, more preferably between 0.25 and 4.5 w/v %. (Each component is expressed in terms of its weight versus the final liquid volume). When either arginine, carnitine, or betaine is used individually their concentrations are between 0.1 and 5.0 w/v %, more preferably between 0.2 and 3.0 w/v %. When arginine and carnitine are mixed together their individual concentrations are also in this range. The ratio between arginine and carnitine is preferably between 0.8 and 1.0, more preferably between 0.85 and 0.90. When serum albumin is used its concentration is between 0.25 and 5.0 w/v %, more preferably between 0.5 and 3.0 w.v %. The preferred vitamin, polymer, or fatty acid concentration is between 0 and 10 w/v %, more preferably between 1 and 5 w/v %, most preferably between 1 and 3%. The preferred concentration of the salt of a low molecular weight organic acid is between 0 and 1 M, more preferably between 0.05 and 0.5 M, most preferably between 0.1 and 0.3 M. See U.S. Pat. No. 5,078,997, the content of which is hereby incorporated by reference.

Sugars or sugar alcohols can be included in the IL-2 compositions. Sugar is defined as mono, di, or polysaccharides, or water-soluble glucans, including for example, fructose, glucose, mannose, sorbose, xylose, maltose, lactose, sucrose, dextran, pullulan, dextrin, cyclodextrin, soluble starch, hydroxyethyl starch, and carboxymethylcellulose-Na. Sucrose is the most preferred sugar. Sugar alcohol is defined as a C4–C8 hydrocarbon having an —OH group and includes for example mannitol, sorbitol, inositol, galactitol, dulcitol, xylitol, and arabitol, mannitol being the most preferred. The sugars or sugar alcohols mentioned above may be used individually or in combination. There is no fixed limit to the amount used as long as the sugar alcohol is soluble in the aqueous preparation. Preferably, the sugar or sugar alcohol concentration is between 1.0 w/v % and 7.0 w/v %, more preferably between 2.0 and 6.0 w/v %.

It also is preferred to use a buffer in the composition to minimize pH changes in the solution before lyophilization or after reconstitution. Most any physiological buffer may be used, but citrate, phosphate, cuccinate, or glutarate buffers, or mixtures thereof are preferred. Most preferred is a citrate buffer. Preferably, the concentration is from 0.01 to 0.3 M.

Controlled release formulations also are envisioned by the present invention. For example, there is a great deal of literature on liposomes that are useful to deliver proteins, specifically IL-2. In this regard, the contents of the following U.S. Pat. Nos. are hereby incorporated by reference: 4,863,740, 4,877,561, 5,225,212, 5,007,057, 5,049,389, 5,023,087, 4,992,271, 4,962,091, 4,895,719, 4,855,090, 4,844,904, 4,781,871, 4,762,720, 4,752,425, 4,612,007, 5,292,524, 5,258,499, 5,229,109, 4,983,397, 4,895,719, and 4,684,521.

Additionally, the use of multivesicullar vesicles and microcapsules also are envisioned by the present invention, see WO 94/23697 and U.S. Pat. No. 5,102,872 respectively. IL-2 may be entrapped or conjugated to polymers and implanted in a patient to facilitate slow release. Examples of these technologies are shown in U.S. Pat. Nos. 5,110,596, 5,034,229, and 5,057,318, the respective contents of which are hereby incorporated by reference. Alternatively, other IL-2 formulations resulting in equivalent immune stimulation for one day to two weeks could be utilized.

Polymer modified IL-2 is useful because it has an increased in vivo half life, reduced immunogenicity and increased solubility. Most importantly, the modification regulates the in vivo clearance so that the IL-2 levels in the body can be regulated. For example, the size of the polymer modified IL-2 can be manipulated so that the IL-2 levels in the body are maintained at optimum levels.

Purified IL-2 may be covalently conjugated to a homopolymer of polyethylene glycol (PEG) or a polyoxyethylated polyol (POP). PEG is soluble in water at room temperature and has the general formula: $R(O-CH_2-CH_2)_nO-R$ where R can be hydrogen, or a protective group such as an alkyl or alkanol group. Preferably, the protective group has between 1 and 8 carbons, more preferably is it methyl. The symbol n is a positive integer, preferably between 1 and 1,000, more preferably between 2 and 500. The PEG has at least one hydroxy group, more preferably it is a terminal hydroxy group. It is this hydroxy group which is preferably activated to react with a free amino group on the IL-2. However, it will be understood that the type and amount of the reactive groups may be varied to achieve a covalently conjugated PEG/IL-2 of the present invention.

Water soluble polyoxyethylated polyols also are useful in the present invention. They include polyoxyethylated sorbitol, polyoxyethylated glucose, polyoxyethylated glycerol (POG), etc.; POG is preferred. One reason is that the glycerol backbone of polyoxyethylated glycerol is the same that occurs in mono-, di-, triglycerides commonly found in animals and humans. Therefore, this branching would not necessarily be seen as a foreign agent in the body. The POG has a preferred molecular weight in the same range as PEG. The structure for POG is shown in Knauf et al., *J. Bio. Chem.* 263: 15064–70 (1988). PEG/IL-2 and POG/IL-2 conjugates are further disclosed in U.S. Pat. Nos. 4,766,106, 4,902,502, 5,089,261, and 5,206,344, the respective contents of which are hereby incorporated by reference along with Knauf et al., supra.

The following discussion is directed to the conjugation of these water soluble polymers to IL-2. It should be understood that even though PEG or POG is mentioned, other water soluble polymers can be used. The PEG or POG is attached to IL-2 by covalent conjugation. "Covalently conjugated" or "conjugated" refer to the covalent linking of PEG or POG to IL-2 via an activated PEG or POG. "Active" or "activated" describes the attachment of a reactive group to a hydroxyl group and then the active molecule is covalently conjugated to an amino group or IL-2. While conjugation may occur between any reactive amino acids on the protein, the reactive amino acid is preferably lysine. The lysine is linked to a reactive group on PEG or POG through its free-amino group.

Processes for covalently conjugating IL-2 to a polymer are described in U.S. Pat. Nos. 4,902,502, 4,766,106, and 5,206,344, the respective contents of which all are hereby incorporated by reference. For example, U.S. Pat. No. 4,902,502, describes a process for linking a polymer to IL-2 via a urethane or carbamate bond. The U.S. Pat. Nos. 4,766,106, and 5,206,344, patents describe covalent conjugation between a polymer and IL-2 through an ester or amide bond. The reaction conditions during the covalent conjugation also are included in those patents referenced above. For example, the molar ratio of activated polymer molecules per mole IL-2 is shown in both references. However, this ratio does depend on the percent activity of the activated polymer. Preferred pH ranges also are disclosed in those references. For example, a pH range from about 5 to 9 is preferred in the U.S. Pat. No. 4,766,106 patent, whereas a pH range between 8 and 10 is preferred in the U.S. Pat. No. 4,902,502 patent. Other parameters such as reaction time, buffers, purification procedures, characterization procedures, assay procedures, and formulations are further disclosed in these two references, the respective contents of which are hereby incorporated by reference.

In sum, formulations of IL-2 that are useful in the present invention include native IL-2 protein, recombinant IL-2, and sustained release forms of IL-2, such as polyethylene glycol prepared IL-2 (PEG IL-2), liposomal IL-2, and microencapsulated IL-2.

It is anticipated that any method of administering IL-2 that mimics the above-described cycle of (a) periods of administration followed by (b) intervals with no administration will have the beneficial effects of the present invention. For example, IL-2 may be administered according to this regimen via continuous infusion, bolus injection, or by constant infusion. Additionally, IL-2 may be injected parenterally, intravenously, intraperitoneally, intraarterially, subcutaneously, or intradermally. Also, it may be inhaled as an aerosol. See EP 257,956, Huland et al., *J. Urology,* 147: 344–348 (1992), and Huland et al. *J. Cancer Res. Clin. Oncol.* 120: 221–228 (1994). Also, IL-2 may be administered by a pump. Examples of pumps are shown in U.S. Pat. Nos. 4,320,758, 4,976,966 and 3,929,132, the respective contents of which are hereby incorporated by reference. Computer programs also may be used to drive the pumps and to administer the proper concentration of IL-2. Computer programs designed for this purpose are within the skill of the art.

The intermittent administration of IL-2 may be analogous to the in vitro approach of alternating cycles of stimulation with rest that is needed for the establishment or expansion of T-cell lines or clones. M. Kimoto & G. G. Fathman, *J. Exp. Med.* 152: 759–70 (1980). It is possible that IL-2 also could prolong T-cell survival by altering HIV-envelope mediated programmed cell death, which may play a role in CD4 depletion in HIV infection. D. I. Cohen et al., *Science* 156: 542–45 (1992); H. Groux et al., *J. Exp. Med.* 175: 331–40 (1992). Additionally, IL-2 may be altering the balance between Th1 and Th2 lymphocytes, and thus reversing the relative deficiency of Th1 cells that has recently been suggested to occur in HIV infection. H. C. Lane et al., *N. Engl. J. Med.* (1984); M. Clerici et al., *J. Clin. Invest.* 91: 759–65 (1993).

Present studies have focused on treating HIV-infected patients with a relatively intact immune system. The degree of response of the patient to the treatment has been shown to be directly correlated to the level of immune system remaining in the patient, or inversely related to the level of the virus in the patient. The degree of remaining immune system can be measured by the T4 or CD4 count of the patient. Patients with a T4 or CD4 count above about 150 cells/mm$^3$ were found to respond well to the method of treatment of the present invention. The level of virus in the patient can be measured by viral titer. If the plasma contains more than about 10,000 copies of HIV genomic RNA/ml, the patient is not recommended for immediate treatment without concomitant anti-retroviral therapy. Assays to detect viral load (bDNA) are shown in U.S. Pat. Nos. 4,868,105 and 5,124,246, the respective contents of which are hereby incorporated by reference.

Patients with viral levels that are too high can be first treated with ddI, AZT, or other anti-retroviral drugs to lower the viral burden. Alternatively, the anti-retroviral therapy can be administered simultaneously with the IL-2 therapy, allowing patients with weaker immune systems and higher viral burdens to benefit from the intermittent IL-2 therapy.

Another reason for administering concomitant anti-retroviral therapy to AIDS patients undergoing IL-2 therapy is the major concern that the viral burden of HIV patients receiving IL-2 therapy will be increased, since retroviruses infect and HIV replicates more readily in activated cells. To minimize the possible effects of increased viral burden, the IL-2 therapy is preferably combined with an anti-retroviral therapy. Such anti-retroviral therapy can comprise, for example, the administration of AZT, AZT and ddI, or interferon alpha. The anti-retroviral therapy can commence before the IL-2 therapy is started, and can continue throughout the course of the intermittent IL-2 therapy. When patients with CD4 counts above 150 cells/ml are receiving concomitant anti-retroviral therapy, it appears that increased viral replication occurs only in the brief interval around the infusion of IL-2. In this setting, potent agents, for example, U-90152 (Upjohn), PMEA (Gilead), CD4-PE (Upjohn), protease inhibitors available from Merck or Abbot, or zinc finger inhibitors may be used intermittently for short periods of time without the development of resistant strains of virus.

Figure 21A:
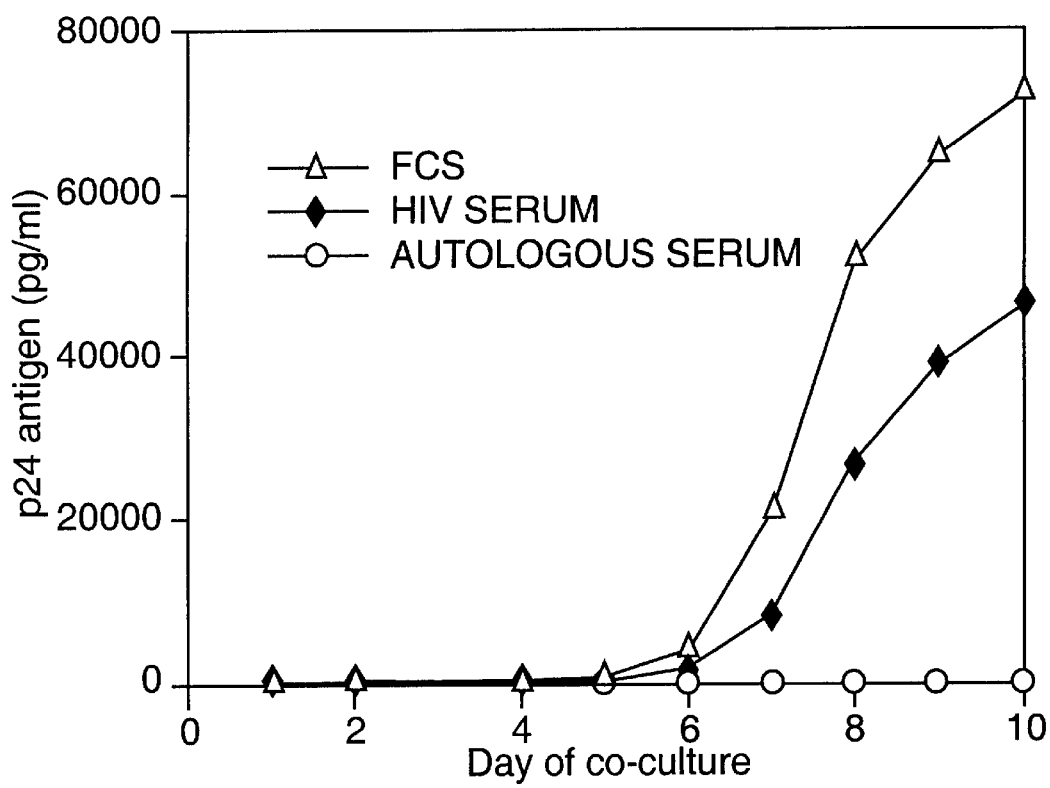
FIG. 21A shows the HIV-neutralizing activity of autologous serum as demonstrated by a p24 assay.
Figure 21B:
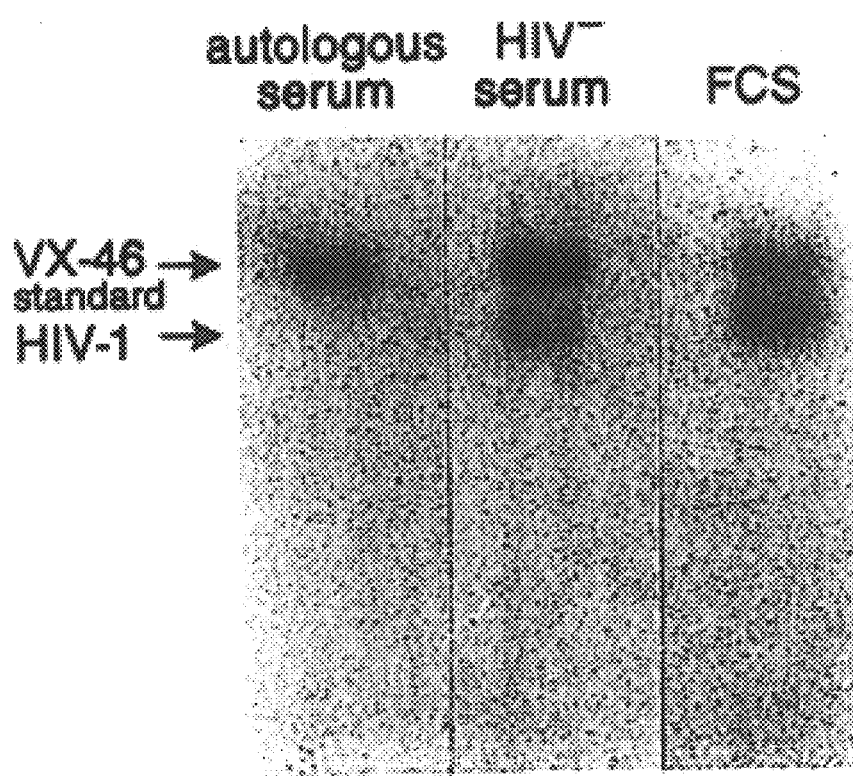
FIG. 21B is an autoradiograph of a quantitative PCR of the samples plotted in FIG. 21A.

It is contemplated that monoclonal or polyclonal anti-HIV antibodies could be administered around or during the period of IL-2 infusion effectively to block the viral burst of HIV which IL-2 can induce. FIGS. 21A and 21B demonstrate the ability of anti-HIV antibodies (present in autologous serum of an HIV-infected patient) to neutralize HIV. Fetal calf serum (FCS), serum from an HIV-negative patient (HIV−) and serum from an HIV-positive patient (autologous serum) were cocultured in HIV+PBL with 3-day blasts and assayed for p24 antigen. FIG. 21B is an autoradiograph of $^{32}$P-labeled probe hybridized HIV virion CDNA from internally controlled quantitative PCR of the coculture supernatants. An internal standard of VX-46 virus is shown with the coculture supernatants. Cell culture supernatants containing FCS, HIV− and HIV+ (autologous) serum had 7.66, 7.10 and 5.00 ($log_{10}$) HIV RNA copies per ml, respectively.

Immunoglobulin from different patients and different stages of the disease may be pooled together to prepare an anti-viral preparation. "Cocktails" of different anti-HIV monoclonal antibodies have been administered to animals in tests of preparations for passive immunizations against HIV infection. Boyd et al., *Clin. Exp. Immunol.,* 88: 189–202 (1992); Karwowska et al., *Biotech. Ther.* 2: 31–48 (1991). Similar preparations could be administered around the time of IL-2 administration to decrease viremia.

Figure 12:
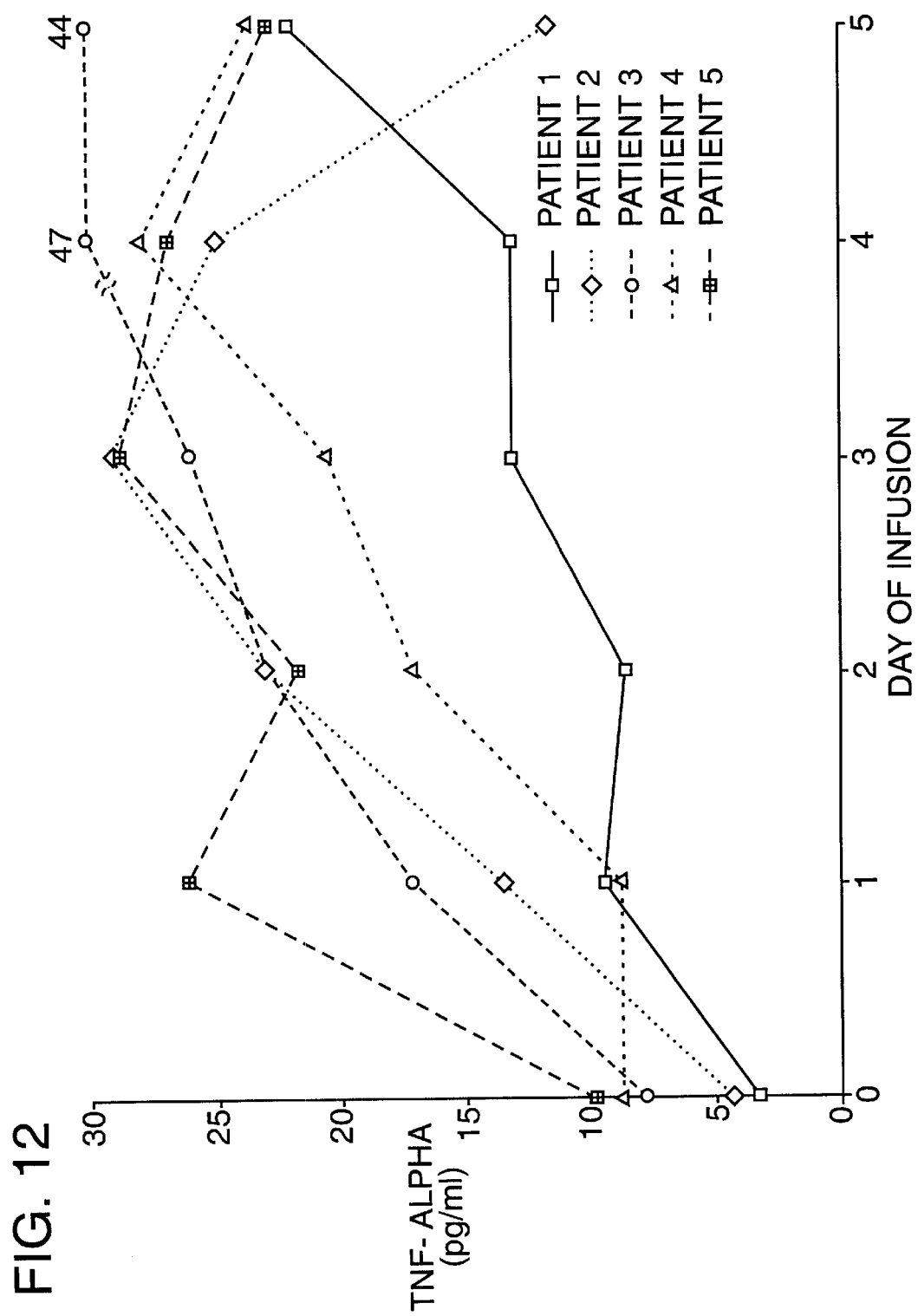
FIG. 12 shows the changes in TNF-alpha levels in five patients during a 5 day infusion of IL-2.
Figure 13:
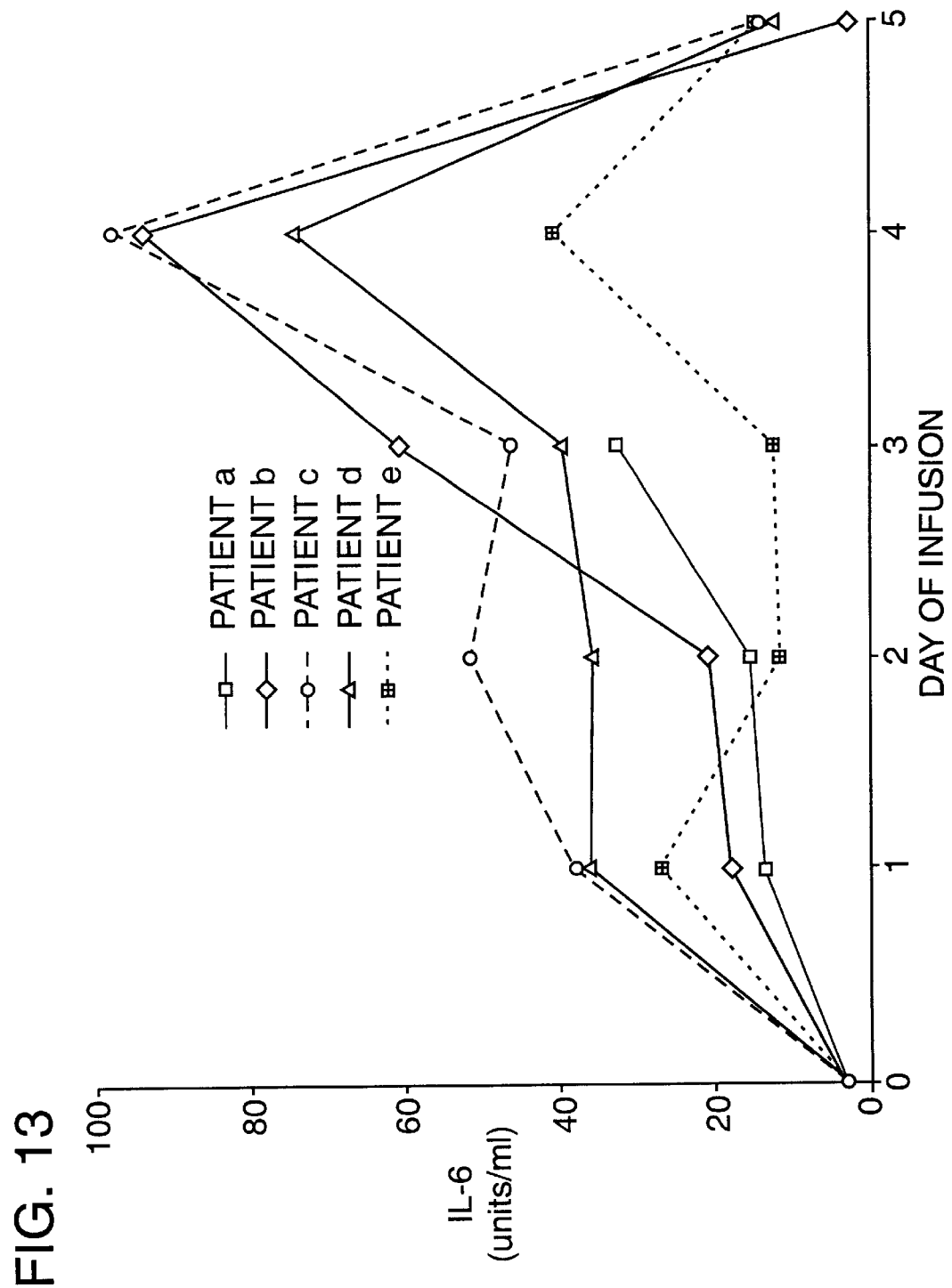
FIG. 13 shows the changes in IL-6 levels in five patients during a 5 day infusion of IL-2.

The side effects of IL-2 administration, including the increased replication of HIV, appear to be related to the induction of pro-inflammatory cytokines, such as tumor necrosis factor (TNF) and interleukin-6 (IL-6). (See FIGS. 12 and 13.) By administering compounds that block the activity of these cytokines, such as pentoxyfyllin, thalidomide, anti-TNF antibodies, or soluble forms of the TNF receptor molecule, the severity of the side effects and/or the increased replication of HIV may be reduced.

Figure 14A:
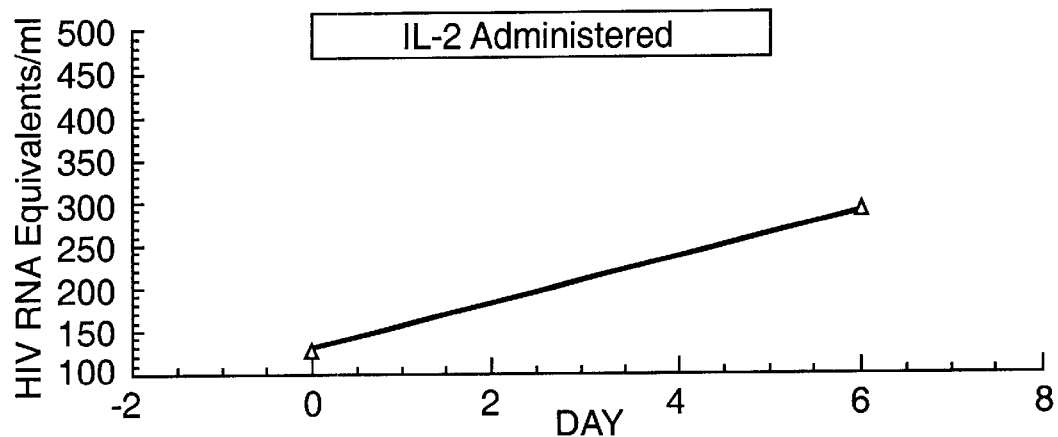
FIGS. 14A and 14B show that the administration of a protease inhibitor concomitantly with the administration of IL-2 blocks the induction of virus otherwise observed during IL-2 administration.
Figure 14B:
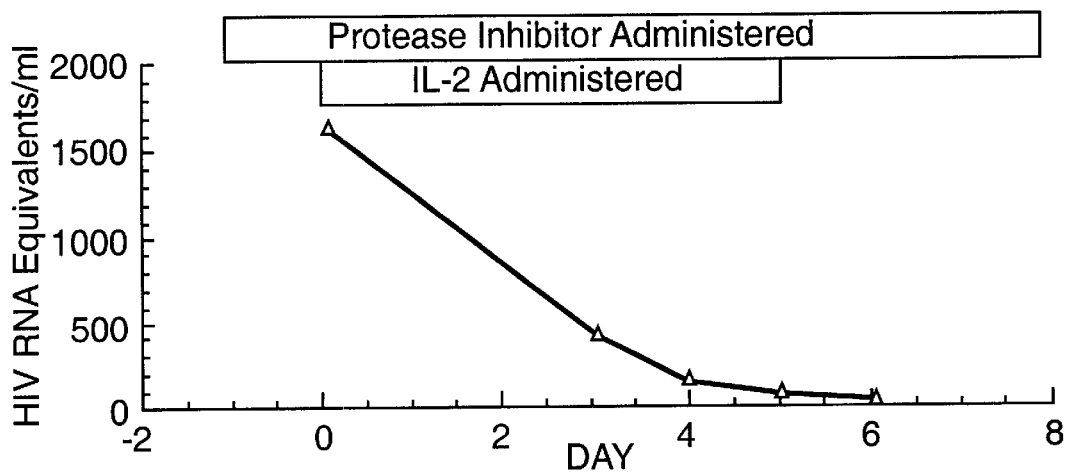
Figure 15A:
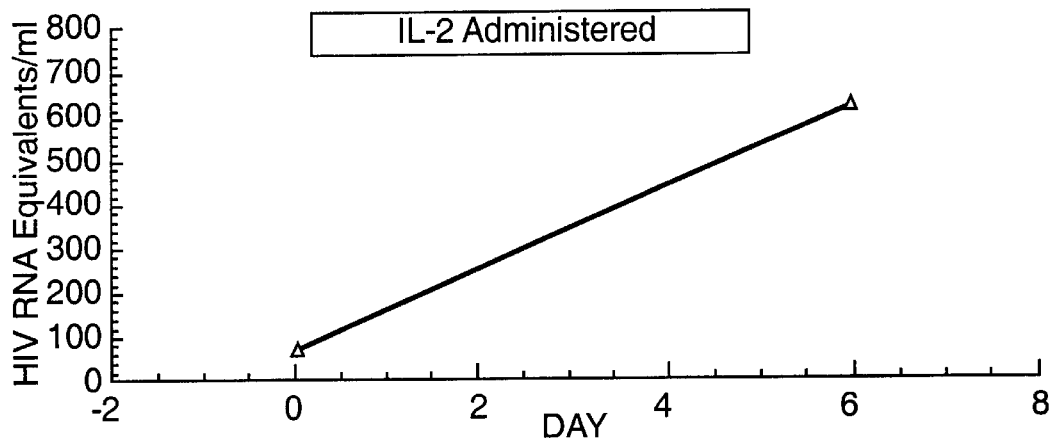
FIGS. 15A and 15B show that the administration of delavirdine concomitantly with the administration of IL-2 blocks the induction of virus otherwise observed during IL-2 administration.
Figure 15B:
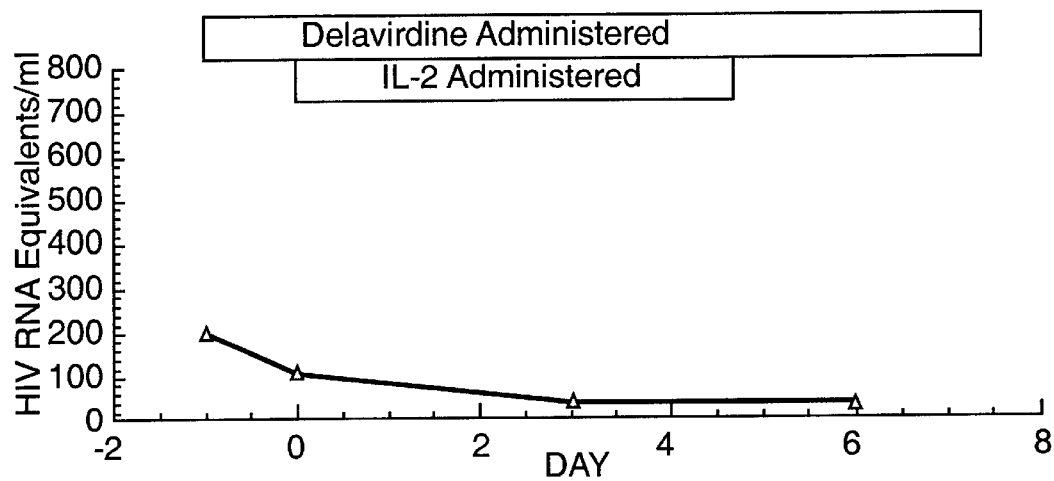

As better anti-retroviral drugs are identified, the intermittent IL-2 therapy of the present invention may be further enhanced by the use of these agents to block the replication of HIV in general, and to block the viral burst induced by IL-2 in particular. The administration of a combination of anti-retroviral drugs during the time of IL-2 administration may be particularly advantageous. FIGS. 14A and 14B show that the administration of a drug to which the patient is naive (a protease inhibitor) was able to completely block the induction of virus during IL-2 administration. FIGS. 15A and 15B show that the administration of delavirine, a non-nucleoside reverse-transcriptase inhibitor, also was able to completely block the induction of virus during IL-2 administration. IL-2 could be used as an early intervention strategy to maintain CD4 counts above a certain level. In this scenario, intensive anti-retroviral therapy only would be given around the time of IL-2 administration.

When the intermittent IL-2 therapy of the present invention is used in the treatment of disease states other than HIV infection, additional therapies which target such disease states also can be used in conjunction with the IL-2 therapy. For example, anti-bacterial agents could be used in the treatment of bacterial infections and anti-fungal agents could be used in the treatment of fungal conditions. As disclosed above with reference to anti-retroviral therapy, such treatments could be used prior to or concomitant with the intermittent IL-2 therapy of the present invention.

Opportunistic infections may also be treated using the present invention. For example, AIDS related opportunistic infections are described in Mills et al. (1990) *Scientific American* 263: 51–57, which is hereby incorporated by reference in its entirety. Mills show that common opportunistic infections are caused by, for example, Cytomegalovirus, Pneumocystis carnii, Candida albicans, Varicella-Zoster virus, Epstein-Barr virus, Toxoplasma gondii, Mycobacterium avium, Cryptococcus neoformans. It is envisioned that IL-2 may be administered along with other compounds used to treat infectious diseases or other diseases. Examples of other agents include antifungal, antiviral, or antibacterial drugs. Additionally, IL-2 may be administered in combination with other efficacious cytokines. For example, combination therapy may include IL-2 with GM-CSF, G-CSF, M-CSF, IL-3, IL-12, IL-15, a-, b-, or g-interferons.

Examples of antifungal agents include Amphotericin B, Fluconazole (Diflucan), 5 fluro-cytosine (Flucytosine, 5-FC), Ketoconazole, Miconazole, and Intraconazole. Examples of antibacterial agents include antibiotics, such as those selected from the following categories: beta lactam rings (penicillins), amino sugars in glycosidic linkage (aminoglycosides), macrocyclic lactone rings (macrolides), polycyclic derivatives of napthacenecarboxamide (tetracyclines), nitrobenzene derivatives of dichloroacetic acid, peptides (bacitracin, gramicidin, and polymyxin); large rings with a conjugated double bond systems (polyenes), sulfa drugs derived from sulfanilamide (sulfonamides), 5-nitro-2-furanyl groups (nitrofurans), quinolone carboxylic acids (i.e. nalidixic acid), and many others. The groups of antibiotics mentions above are examples of preferred antibiotics, examples of antibiotics within those groups are: peptide antibiotics, such as amphomycin, bacitracin, bleomycin, cactinomycin, capreomycin, colistin, dactinomycin, enduracidin, gramicidin A, gramicidin J (S), mikamycins, polymyxins, stendomycin, thiopeptin, thiostrepton, tyrocidines, viomycin, virginiamycins, and actinomycin, aminoglycosides, such as streptomycin, neomycin, parommycin, gentamycin, ribostamycin, tobramycin, amikacin, lividomycin beta lactams, such as benzylpenicillin, methicillin, oxacillin, hetacillin, piperacillin, amoxicillin, and carbenicillin; chloramphenicol; lincosaminides, such as clindamycin, lincomycin, celesticetin, desalicetin; macrolides, such as erythromycins A-E, lankamycin, leucomycin, and picromycin; nucleosides, such as 5-azacytidine, amicetin, puromycin, and septacidin; oligosaccharides, such as curamycin, and everninomicin B; phenazines, such as myxin, lomofungin, and iodin; polyenes, such as amhotericins, candicidin, and nystatin; polyethers; tetracyclines, such as chlortetrayclines, oxytetracycline, demeclocycline, methacyclines, doxycyclines, and minocyclines; sulfonamides, such as sulfathiazole, sulfdiazine, sulfapyrazine, sulfanilimide; nitrofurans, such as nitrofurazone, furazolidone, nitrofurantoin, furium, nitrovin, and nifuroxime; and quinolone carboxylic acids, such as nalidixic acid, piromidic acid, pipemidic acid, and oxolinic acid. *Encyclopedia of Chemical Technology,* 3rd edition, Kirk-Othmer editors, Volume 2, (1978), which is hereby incorporated by reference in its entirety.

Antiviral agents can include: amantadine, rimantadine, arildone, ribaviran, acyclovir, 9-[1,3-dihydroxy-2-propoxy) methyl]guanine (DHPG), vidarabine (ARA-A), ganciclovir, enviroxime, foscarnet, interferons alpha, beta and gamma, ampligen, podophyllotoxin, 2,3-dideoxycytidine (DDC), iododeoxyuridine (IDU), triflorothymidine (TFT), dideoxyinosine (ddi), d4T, 3TC, zidovudine, protease inhibitors, and specific antiviral immune globulins. Sanford, J. P., *Guide to Antimicrobial Therapy,* (West Bethesda Antimicrobial Therapy, Inc., 1989), pages 88–93; and *Harrison's Principles of Internal Medicine,* 11th Edition, Braunwald, E. et al., Eds., (McGraw-Hill Book Co., 1987) pages 668–672.

Progress achieved by IL-2 therapy within the present invention can be measured by many parameters. The IL-2 agent of the present invention increases the number of helper/inducer T cells and boosts the helper/inducer T-cell function of the cells. The helper T-cells activate various T effector cells that generate cell-mediated responses to antigens, including an increased production of IL-2 and IL-2 receptors. See J. Kuby, IMMUNOLOGY 17–18, W. H. Freeman and Co. (1992). The increase in IL-2 receptors observed in patients undergoing therapy by this method is consistent with such an elevation of helper/inducer T-cell function.

Studies have shown that in HIV-infected patients, responses of peripheral blood lymphocytes, as measured by lymphocyte blast transformation as well as by IL-2 production, tend to be lost initially to recall antigens, then to alloantigens, and finally, as immunosuppression becomes severe, to mitogens such as phytohemagglutinin and pokeweed mitogen. M. T. Lotze et al., *Cancer* 58: 2754–2772 (1986); H. C. Lane et al., *New England J. Med.* 313: 79–84 (1985); M. Clerici et al., *J. Clin. Invest.* 91: 759–65 (1993). Although the decreased responses to alloantigens and mitogens may be at least partially explained by alteration in relative numbers of CD4 and CD8 cells placed in tissue culture, this defect in responsiveness to soluble antigens is seen even when one studies purified CD4 cells. H. C. Lane et al., *New England J. Med.* 313: 79–84 (1985). In fact, one of the earliest immune defects associated with HIV infection is this loss of ability to respond to recall antigens, and is often present in patients with normal CD4 counts. H. C. Lane et al., *New England J. Med.* 313: 79–84 (1985).

The ability of intermittent IL-2 therapy to restore in vitro lymphocyte function has been determined. As shown in Table 2 and FIG. 1, intermittent IL-2 therapy pursuant to the present invention has been associated with an improvement in blastogenic responses in the reverse order of their probable loss.

Another phenomenon observed in HIV patients is the increased percent of human leukocyte antigen-D related-positive (HLA-DR-positive) lymphocytes compared to healthy controls. A. Landay et al., *AIDS* 4: 479–497 (1990); J. V. Giorgi et al., *Clin. Immunol. Immunopathol* 52: 10–18 (1989). This represents an increase in the proportion of lymphocytes in the peripheral blood that are activated and presumably terminally differentiated. This increase in HLA-DR is seen primarily in CD8 positive cells, and may be a poor prognostic sign. D. P. Sites et al., *Clin. Immunol.*

*Immunopathol* 38: 161–77 (1986). The percent of HLA-positive lymphocytes of all patients were found to be elevated prior to treatment.

As shown in FIG. 2 and Table 2, the intermittent IL-2 therapy of the present invention leads to a decline in the proportion of cells positive for HLA-DR. This decline in HLA-DR positive cells may represent an IL-2-induced improvement in the aberrant homeostatic mechanisms that are regulating CD8 lymphocyte activation in HIV. These decreased levels are observed even one and two months after completion of IL-2 courses. The disappearance of aberrantly activated cells from the peripheral blood suggests that the immune system is working more normally. These cells are not only active, therefore, they are performing their normal function, which usually results in their death.

Levels of IL-2 receptors in CD4 positive cells and in both CD4 and CD8 cells increased during the intermittent IL-2 therapy. This up-regulation of IL-2 receptors is likely a pharmacologic effect of IL-2, and may explain why some patients had increases in CD4 but not CD8 cells, while other patients had increases in both. It is our belief that by monitoring changes in IL-2 receptor expression on these cell types it should be relatively easy to target either CD4 or CD8 cells ;for expansion. The increase in IL-2 receptor-expressing cells also may be responsible for the improvement in blastogenic responses, since such responses are dependent on recruitment of initially unresponsive cells, and such cells, if expressing IL-2 receptors, can respond more easily to IL-2 secreted by the initially activated cells.

Our observations differ from other reports using low doses of recombinant IL-2 or polyethylene glycol IL-2 subcutaneously, in which no changes in CD4, CD8, HLA-DR, or IL-2 receptor-positive cells were seen (H. Teppler et al., *J. Infect. Dis.* 167: 291–298 (1993); H. Teppler et al., *J. Exp. Med.* 177: 483–492 (1993)). Further, while natural killer (NK) activity has been shown to increase with low doses of IL-2 (H. Teppler et al., *J. Infect. Dis.* 167: 291–298 (1993); M. A. Caligiuri et al., *J. Clin Invest.* 91: 123–132 (1993)), we observed no consistent changes in NK or LAK activity following IL-2 therapy (data not shown).

A therapy which targets a specific disease state may be administered prior to, concomitant with, or subsequent to the IL-2 administration. Illustrative disease states include HIV infection, mycobacterial infections such as tuberculosis, and fungal infections such as cryptococcal disease. For example, the therapy may be an anti-retroviral therapy such as zidovudine, ddI or interferon alpha administration.

Another aspect of the present invention is retroviral therapy. In this embodiment of the invention, IL-2 is administered as described above to activate the immune system, and a retroviral vector is administered to effect an in situ transformation of lymphocytes. In contrast to prior art methods of gene therapy where cells are obtained from the patient, transduced in vitro, and infused into the patient, the present invention allows the direct administration of a retroviral vector to the patient, with the transduction of the cells occurring in situ.

In this embodiment of the present invention, the immune system is first activated by administering IL-2 as described above. The IL-2 induces the cells to become activated and to synthesize DNA, which makes them more receptive to transduction by retroviral vectors. A genetically-engineered retroviral vector then is administered directly to the patient. Retroviral vectors that would make a cell resistant to a virus or that would make a cell able to attack a virus could be introduced into a patient's system by this method. For example, this vector may contain a retrovirus that encodes a T-cell receptor with specificity towards a targeted species, such as HIV, cytomegalovirus or pneumocystys carinii.

The vector is integrated with the DNA of the patient's own cells, and the administered gene is subsequently expressed. Plasmid DNA can be used in place of the retroviral vectors, with similar benefits and results seen. This therapy may be repeated indefinitely as long as an interval is provided after each course of IL-2 administration before the next course of IL-2/vector administration.

The known methods of in vitro transduction can be adapted for use in accordance with the present invention. That is, the same vectors that are used for in vitro transduction can be used for in situ transduction in accordance with the present invention. For example, the in vivo transduction method of the present invention could be implemented with the vectors described in Roberts et al., *Blood* 84(9): 2878 (1994), in the context of in vitro transduction of cells for targeting HIV. The contents of the Roberts et al. article are incorporated by reference.

The present method is most effective when the vector is administered to the patient when cells are most susceptible to transduction by the vector. Such susceptibility occurs during periods of peak DNA synthesis, which is usually observed during the time period when the IL-2 is being administered.

FIG. 4 shows the levels of DNA synthesis occurring in vivo in seven patients receiving a 5-day continuous infusion of IL-2 at the above described dosages. Data points were taken prior to IL-2 therapy (PRE), at day 0 of the IL-2 infusions (D/0), at day 5 (D/5) of the IL-2 infusions, and at follow-up visits (F/U). Each peak corresponds to the level of DNA synthesis at day 5 of infusion. This intense in vivo T-cell activation seen at day 5 of the IL-2 infusion marks a preferred time to effect T-cell transduction by administering a retroviral vector directly to the patient.

FIG. 7 shows the daily branched DNA (bDNA) levels for selected patients undergoing intermittent IL-2 therapy in accordance with the invention. This Figure illustrates the peak in bDNA levels around day 5 of IL-2 infusion, which marks a preferred time to effect T-cell transduction by administering a retroviral vector to the patient.

The branched DNA assay is a monitor of viral activity that quantitatively measures HIV RNA. The increase in measured bDNA levels during periods of IL-2 infusion reflects an increase in spread of HIV following an increase in lymphocyte activity. This IL-2-induced heightened level of lymphocyte activity marks a preferred time to effect the in situ transformation of T-cells by a retroviral vector. In particular, the administration of IL-2 activates the cells, and induces them to produce DNA. It is during these times of peak DNA synthesis that the cells are most susceptible to transduction.

Also encompassed by the present invention are kits for performing the above described methods. For example, kits may comprise a liquid preparation comprising an amount of IL-2 in a pharmaceutically acceptable carrier and directions for administering the IL-2 in accordance with the intermittent therapy of the present invention. A component is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.); REMINGTON'S PHARMACEUTICAL SCIENCES, 18th Edition (Mack Publishing Company 1990).

The kits also may comprise anti-retroviral agents, or retroviral vectors for the in situ transformation of lymphocytes.

The present invention is further illustrated by reference to the following examples, which illustrate specific elements of the invention but should not be construed as limiting the scope of the invention.

EXAMPLES

Studies of the effects of intermittent courses of IL-2 on the immune system of immunodeficient patients were performed. The studies were approved by the National Institute of Allergy and Infectious Disease (NIAID) institutional review board, and all patients provided written informed consent after the risks of the study had been explained.

Patients with HIV infection were eligible for enrollment if they had a CD4 count above 200 cells/mm$^3$ and had no concurrent opportunistic infections. The cut-off for CD4 counts was selected based on earlier work demonstrating that this group is more likely to respond to immunomodulators than patients with severely impaired immune function.

Because of concerns that IL-2 could lead to enhanced HIV replication, anti-retroviral therapy, primarily zidovudine (AZT), was administered throughout the study. Initial evaluation included a complete history, physical exam, hematology and chemistry profiles, urinalysis, immunologic profiles, p24 antigen levels and, in some patients, titers of plasma virus (Dewar et al., *Acq. Immune Def. Syndromes*, 5: 822–828 (1992)) or quantitation of particle-associated plasma HIV RNA using a branched DNA (bDNA) assay. Dewar et al., *J. Infect. Dis.* (1995); C. A. Pachl et al., Abstract #1247, 32nd INTERSCIENCE CONFERENCE ON ANTIMICROBIAL AGENTS AND CHEMOTHERAPY, October 1992; M. S. Urdea et al., NUCLEIC ACID RESEARCH SYMPOSIUM SERIES No. 24, pages 197–200 (Oxford University Press 1991). Laboratory evaluation was repeated at least monthly.

EXAMPLE 1

Initial Toxicity Trials of Continuous Infusions of IL-2

Native and recombinant IL-2 was administered to patients by continuous infusion at doses up to 12 MU/day for a three-to-eight-week course.

These dosages of IL-2 were well-tolerated, and transient increases in CD4 counts could be seen (H. C. Lane et al., *J. Biol. Response Mod.* 3: 512–516 (1984)). Bone marrow biopsies obtained at the end of this continuous IL-2 therapy demonstrated a relative lymphocytosis when compared to pre-therapy samples, suggesting that effects of IL-2 were not simply the retrafficking of lymphocytes to the peripheral blood.

EXAMPLE 2

Dosage Escalation Trial With Continuous Infusions of IL-2

A dose escalation trial was performed in which 23 patients received a single 21-day or 5-day course of recombinant IL-2 (rIL-2; Chiron) by continuous infusion, at doses ranging from 1.8 million international units (MU)/day to 24 MU/day. All patients received zidovudine (100–200 mg 5id or q4h) beginning at least six weeks prior to the first IL-2 course.

The maximum tolerated dose of recombinant IL-2 when administered for 21 days in combination with zidovudine was found to be 12 MU/day, and when administered for five days in combination with zidovudine was found to be 18 MU/day. Dose-limiting toxicities were similar to those previously associated with recombinant IL-2 therapy alone (J. P. Siegel et al., *J. Clin. Oncol.* 9: 694–704 (1991); M. T. Lotze et al., *Cancer* 58: 2754–2772 (1986)) and included hepatic and renal dysfunction, thrombocytopenia, neutropenia, respiratory distress, and severe flu-like symptoms.

Transient changes were seen in CD4 counts during this phase, but no consistent long-term changes in immune parameters were seen (data not shown). No consistent changes in p24 antigen levels or ability to culture HIV from peripheral blood mononuclear cells were found.

EXAMPLE 3

Intermittent IL-2 Therapy with Continuous Infusions of IL-2

A multiple course study of intermittent IL-2 therapy was performed. Eight patients (six men and two women) received a five-day course of recombinant IL-2 on an inpatient basis by continuous infusion, initially at a dose of 18 MU/day, every eight weeks. Recombinant IL-2 was administered either through a central line IV or a peripheral IV. When peripheral infusions were used, the recombinant IL-2 was placed in 5% dextrose in water ($D_5W$) containing 0.1% albumin. Zidovudine (100 mg bid) was administered concomitantly. Near the end of the study, didanosine therapy (200 mg bid) was also used in two patients.

The employed dosages of IL-2 generally were well-tolerated and were less toxic than the higher dose regimens typically used in cancer therapy. However, six patients required dosage reduction to 12 or 6 MU/day, primarily because of fever and severe flu-like symptoms. Other toxicities, including metabolic abnormalities, hepatic and renal dysfunction, hypothyroidism, thrombocytopenia, and anemia were seen but were mild and not dose-limiting.

Several parameters were used to evaluate results. Changes in lymphocyte subpopulations (CD4 percent and count, CD8 count, CD4:CD8 ratio, lymphocyte count, and CD3 count) following multiple courses of IL-2 therapy were determined. Flow cytometry was performed on Ficoll-Hypaque-separated peripheral blood mononuclear cells by previously described techniques using monoclonal antibodies to CD3 (T cell), CD4 (helper-inducer T cell), and CD8 (suppressor-cytotoxic T cell) (H. C. Lane et al., *Am. J. Med.* 78: 417–422 (1985)). Values used represent the mean of three pre-study values (Pre-IL-2) and the mean of the two latest values obtained four and eight weeks after the most recent course of IL-2. These results are shown in Table 1. The four-week value tended to be higher than the eight-week value for most patients.

TABLE 1

Changes in lymphocyte subsets during IL-2 therapy

| Pt. No. | Sample | CD4 Percent (% positive) | CD4 No. (Cells/mm$^3$) | CD8 No. (Cells/mm$^3$) | CD4:CD8 Ratio | Lymphocyte No. (Cells/mm$^3$) | CD3 No. (Cells/mm$^3$) |
|---|---|---|---|---|---|---|---|
| 1 | Pre-IL-2 | 20 | 458 | 1485 | 0.31 | 2303 | 2096 |
|   | Weeks 49/54 (6 doses) | 57 | 2130 | 1374 | 1.55 | 3768 | 3597 |
|   | Percent Change | 183 | 365 | −7 | 401 | 64 | 72 |
| 2 | Pre-IL-2 | 36 | 660 | 879 | 0.75 | 1846 | 1619 |
|   | Weeks 52/56 (6 doses) | 52 | 690 | 516 | 1.33 | 1338 | 1160 |
|   | Percent Change | 44 | 5 | −41 | 77 | −28 | −28 |
| 3 | Pre-IL-2 | 14 | 233 | 1037 | 0.22 | 1690 | 1407 |
|   | Weeks 56/60 (7 doses) | 18 | 765 | 3383 | 0.23 | 4256 | 4001 |
|   | Percent Change | 32 | 229 | 226 | 1 | 152 | 184 |
| 4 | Pre-IL-2 | 30 | 421 | 632 | 0.68 | 1423 | 1071 |
|   | Weeks 51/56 (7 doses) | 31 | 469 | 625 | 0.82 | 1501 | 1099 |
|   | Percent Change | 4 | 11 | −1 | 21 | 5 | 3 |
| 5 | Pre-IL-2 | 12 | 291 | 1784 | 0.16 | 2483 | 2137 |
|   | Weeks 51/55 (6 doses) | 13 | 276 | 1624 | 0.17 | 2195 | 1865 |
|   | Percent Change | 7 | −5 | −9 | 4 | −12 | −13 |
| 6 | Pre-IL-2 | 19 | 247 | 732 | 0.34 | 1320 | 1087 |
|   | Weeks 56/60 (4 doses) | 28 | 524 | 1035 | 0.71 | 1919 | 1681 |
|   | Percent Change | 47 | 112 | 41 | 110 | 45 | 55 |
| 7 | Pre-IL-2 | 42 | 871 | 776 | 1.12 | 2051 | 1656 |
|   | Weeks 26/31 (4 doses) | 58 | 1494 | 688 | 2.17 | 2575 | 2220 |
|   | Percent Change | 37 | 72 | −11 | 95 | 26 | 34 |
| 8 | Pre-IL-2 | 23 | 188 | 397 | 0.48 | 817 | 568 |
|   | Weeks 21/26 (3 doses) | 25 | 287 | 576 | 0.50 | 1140 | 798 |
|   | Percent Change | 7 | 53 | 45 | 4 | 39 | 40 |

Six of the eight patients showed a consistent and sustained increase of greater than 25% in CD4 number and/or percent (Table 1 and FIG. 1). The most dramatic increase was from 20% and 458 cells/mm$^3$ (mean of 3 values) pre-therapy to 57% and 2130 cells/mm$^3$ (mean of 2 values) one year later, after completion of six courses of recombinant IL-2 (FIG. 1A).

Changes in CD8 number were more variable, and not necessarily concordant with changes in CD4 number. Four patients showed an increase (>25%) in the CD4:CD8 ratio due predominantly to an increase in CD4 cells (Table 1).

The immediate effects of recombinant IL-2 therapy on peripheral blood CD4 count, measured within 24 hours of discontinuation of therapy, were even more dramatic than the long-term effects measured weeks later. Peak CD4 counts of greater than 2000 cells/mm$^3$ were commonly seen, though these increases were transient (data not shown) and probably reflective of redistribution phenomena.

Changes in immunologic parameters were also determined. To evaluate the ability of intermittent IL-2 therapy to restore in vitro lymphocyte function, blastogenic responses to antigens and mitogens were measured. Proliferation assays were performed as previously described (H. C. Lane et al., Am. J. Med. 78: 417–22 (1985)), using a 1:200 dilution of PWM, or 3 μg/ml of tetanus toxoid in six day, tetanus toxoid and pokeweed mitogen induced lymphocyte blast transformation assays. Values used represent the mean of three pre-study values (Pre-IL-2) and the mean of the two latest values obtained four and eight weeks after the most recent course of IL-2. The results are shown in Table 2 as net CPM of incorporated [3H]-thymidine. Percent of cells positive for IL-2 receptor (IL-2r) and human leukocyte antigen-D related (HLA-DR) expression were determined by multiple-color fluorescent activated cell sorter (FACS) analysis using monoclonal antibodies to CD25 (p55 IL-2 receptor) and HLA-DR. FACS analysis was gated for lymphocytes. These results are also presented in Table 2.

TABLE 2

Changes in markers of lymphocyte function and activation during IL-2 therapy

| Pt. No. | Sample | Tetanus (CPM) | PWM (CPM) | IL-2r (% positive) | HLA-DR (% positive) |
|---|---|---|---|---|---|
| 1 | Pre-IL-2 | 2003 | 1757 | 8 | 43 |
|   | Weeks 49/54 (6 doses) | 8479 | 5981 | 53 | 23 |
|   | Percent Change | 323 | 240 | 585 | −47 |
| 2 | Pre-IL-2 | 118 | 1762 | 5 | 50 |
|   | Weeks 52/56 (6 doses) | 4250 | 12321 | 33 | 31 |
|   | Percent Change | 3512 | 599 | 509 | −38 |
| 3 | Pre-IL-2 | 212 | 1043 | 5 | 35 |
|   | Weeks 56/60 (7 doses) | 100 | 5760 | 30 | 16 |
|   | Percent Change | −53 | 452 | 500 | −56 |
| 4 | Pre-IL-2 | 117 | 1195 | 8 | 32 |
|   | Weeks 51/56 (7 doses) | 100 | 14216 | 23 | 22 |
|   | Percent Change | −15 | 1090 | 176 | −31 |
| 5 | Pre-IL-2 | 100 | 1386 | 5 | 47 |
|   | Weeks 51/55 (6 doses) | 483 | 1980 | 8 | 42 |
|   | Percent Change | 383 | 43 | 60 | −11 |
| 6 | Pre-IL-2 | 1735 | 4720 | 10 | 32 |
|   | Weeks 56/60 (4 doses) | 895 | 5944 | 25 | 30 |
|   | Percent Change | −48 | 26 | 150 | −9 |
| 7 | Pre-IL-2 | 32054 | 12568 | 8 | 21 |
|   | Weeks 26/31 (4 doses) | 39708 | 14041 | 36 | 13 |
|   | Percent Change | 24 | 12 | 326 | −38 |
| 8 | Pre-IL-2 | 121 | 19103 | 8 | 20 |
|   | Weeks 21/26 (3 doses) | 100 | 7878 | 26 | 19 |
|   | Percent Change | −17 | −59 | 206 | −3 |

As shown in Table 2 and FIG. 1, IL-2 therapy was associated with an improvement in blastogenic responses in the reverse order of their probable loss. Thus, four of five (80%) patients with absent or poor responses to PWM developed vigorous and consistent responses during the study, and two of the seven non-responders (29%) to the recall antigen tetanus toxoid became consistent responders.

The percent of lymphocytes positive for HLA-DR was found to be elevated (>20%) in all eight patients prior to study (Table 2). Interestingly, during IL-2 therapy, there was a decline (>25% of initial values) in the proportion of cells positive for HLA-DR, measured one and two months after completion of IL-2, in 5/8 patients (Table 2 and FIG. 2). At the same time, the proportion of cells positive for the IL-2 receptor (IL-2r) (p55) increased progressively (Table 2 and FIG. 2) in all patients. In one patient, this increase was minimal (Patient 5, Table 2) and in this patient there was little evidence of improvement in CD4 counts or blastogenic responses. This same patient also showed only a minimal decrease in the proportion of cells positive for HLA-DR.

Figure 2A:
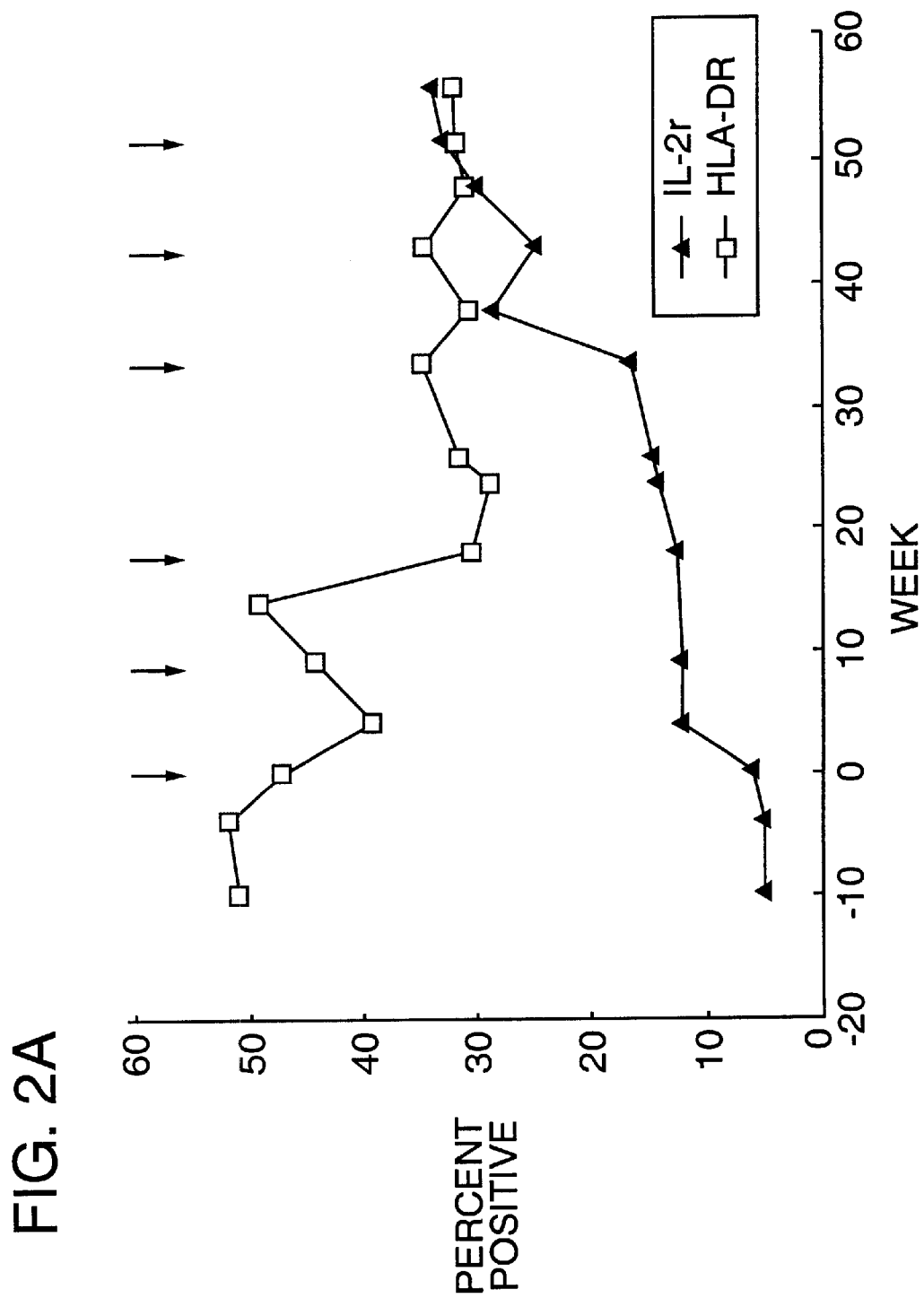
FIG. 2A shows changes in lymphocyte cell surface expression of IL-2 receptors (CD25) and human leukocyte antigen-D related (HLA-DR) expression for patient 2 during a year of IL-2 therapy.
Figure 2B:
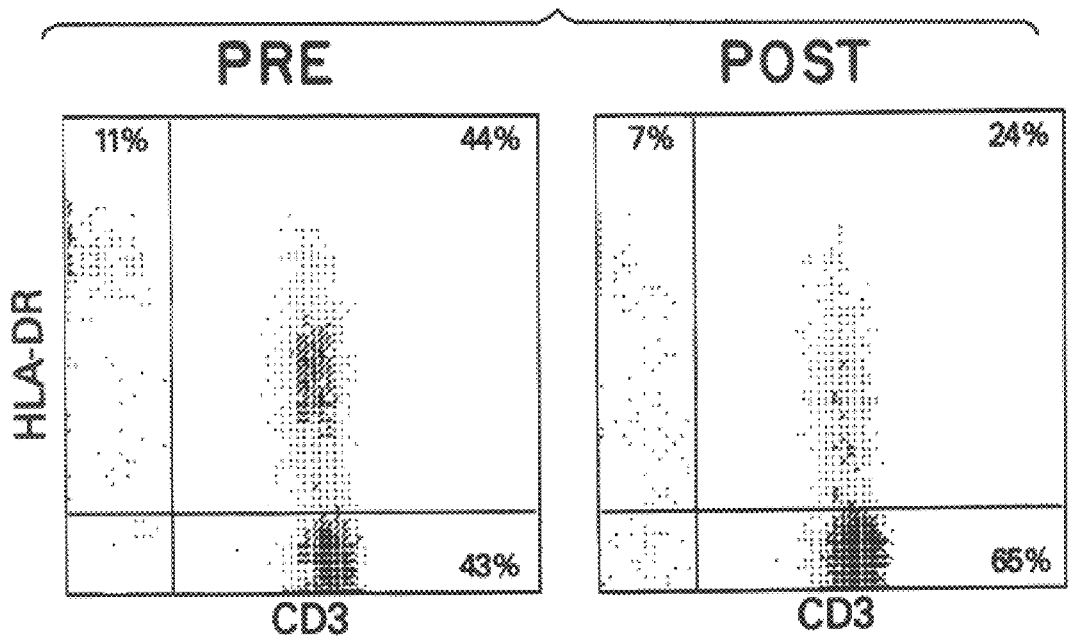
Figure 2C:
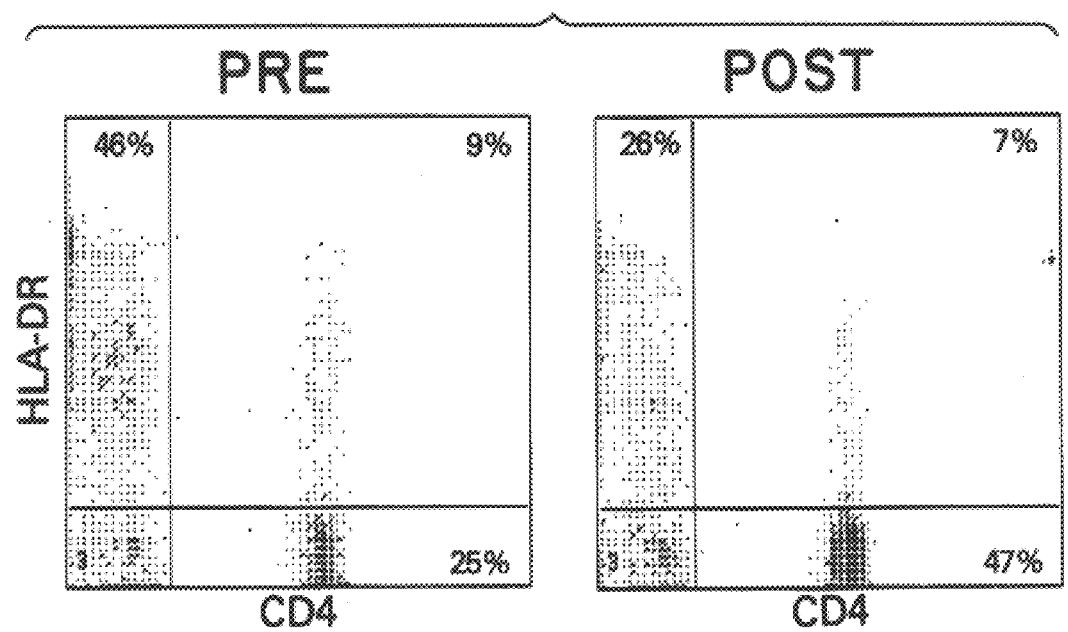
Figure 2D:
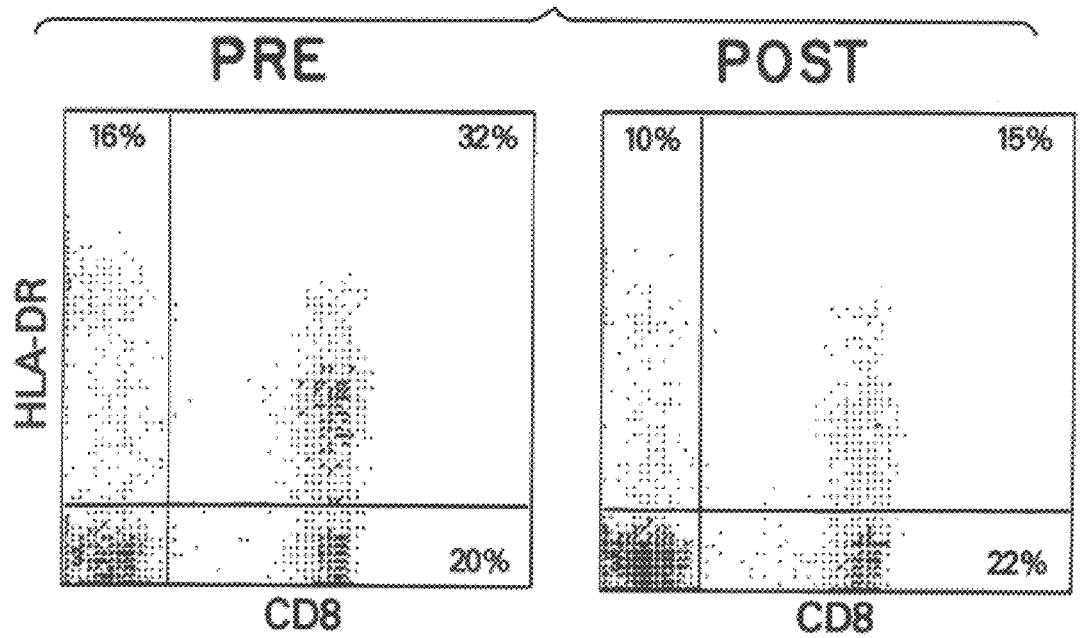
Figure 2E:
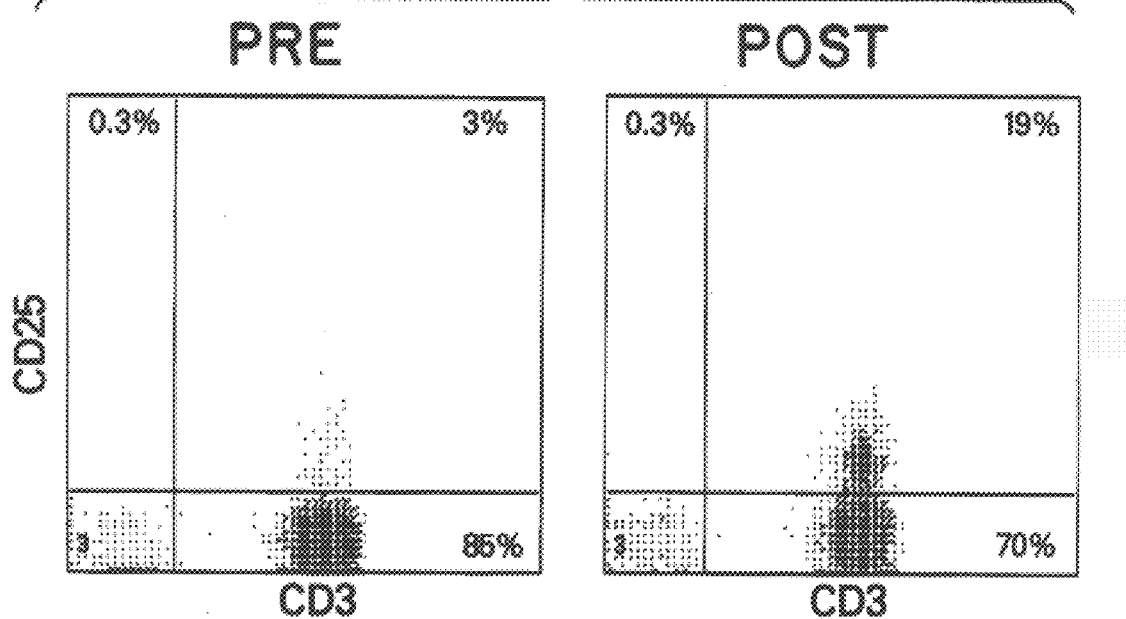

Based on two-color FACS analysis in three patients, CD8 positive cells were the predominant population positive for HLA-DR prior to study, and were the primary population accounting for the decline in this marker (FIG. 2B). IL-2 receptors (IL-2r) increased during IL-2 therapy almost exclusively in CD4 positive cells in patients 1 and 2 (FIG. 2B), while patient 3 showed an increase in IL-2r in both CD4 and CD8 cells. This up-regulation of IL-2r is likely a pharmacologic effect of IL-2, and may explain why patients 1 and 2 had increases in CD4 but not CD8 cells, while patient 3 had increases in both.

FIGS. 1–3 show additional results for the individual patients.

FIG. 1 shows changes in CD4 cell count and blastogenic responses to tetanus toxoid and PWM for patients 1 and 3 during a year of intermittent IL-2 therapy. Arrows indicate the start of each five-day course of continuous infusion IL-2 at an initial dose of 18 MU over 24 hours. Values shown represent results obtained four and eight weeks after each course of IL-2 with the week eight sample drawn immediately before beginning the next round of IL-2.

Figure 1B:
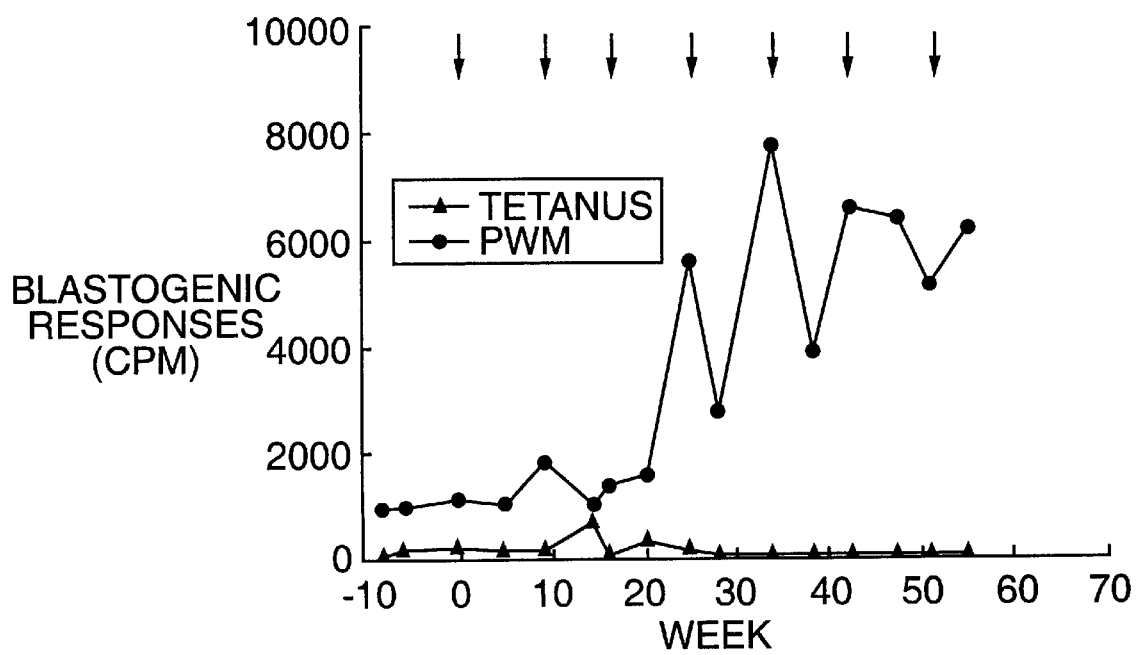

FIGS. 1A and 1B show the results for Patient 1, who demonstrated a marked increase in CD4 cells as well as sustained improvement in lymphocyte blast transformation to both stimuli. The last data point is 15 weeks after the sixth course of IL-2 (week 59) at which point the patient's CD4 count remained above 1500 cells/mm$^3$.

Figure 1C:
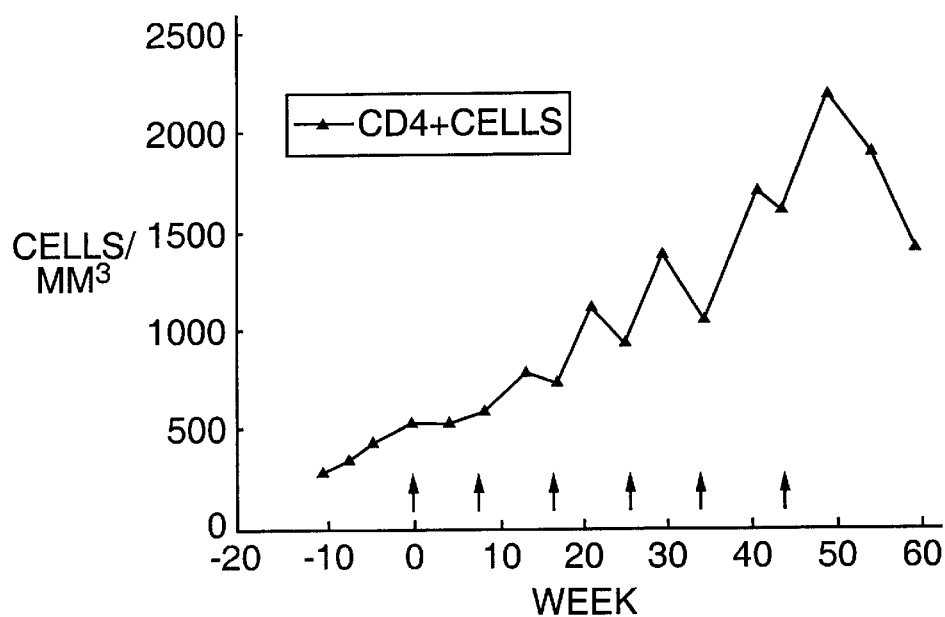
Figure 1D:
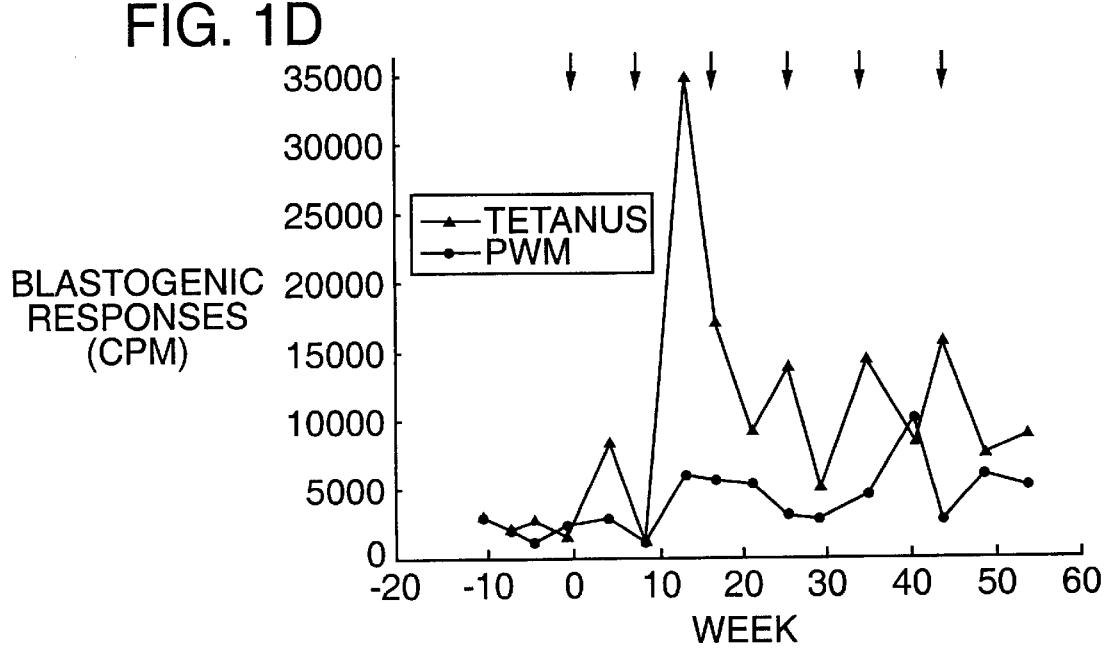

FIGS. 1C and 1D show the results for patient 3, who demonstrated improvement in lymphoid blast transformation to PWM, but not tetanus toxoid. His CD4 count remained stable until after the sixth course of IL-2, at which time it increased. Didanosine was added to this patient's anti-retroviral regimen at week 38.

FIG. 2A shows changes in lymphocyte cell surface expression of IL-2 receptors (CD25) and HLA-DR for patient 2 during a year of IL-2 therapy. Results shown were obtained by single-color FACS analysis using monoclonal antibodies as described in Table 2, on samples obtained four and eight weeks after a course of IL-2. Arrows indicate the beginning of each course of IL-2. A sustained drop in the percentage of HLA-DR positive cells began after the second course of IL-2. The percentage of IL-2 receptor-positive cells increased substantially after four courses of IL-2.

FIGS. 2B–2G show two-color FACS analysis of IL-2 receptor (IL-2r) and HLA-DR expression determined on frozen cells of patient 2 obtained prior to IL-2 therapy, and at week 48 (five weeks after the fifth course of IL-2). As shown, the increase in IL-2r in this patient was due to increased expression exclusively on CD4 cells, while the decline in HLA-DR expression was due primarily to a decrease in expression on CD8 cells. Normal values for CD3+/IL-2r+ cells are 4.4±1.5%, and for CD3+/HLA-DR+ cells are 8.7±2.9%.

FIGS. 3A–3J show changes in viral markers during IL-2 therapy for patients 2, 3, 4, 6 and 8. Results are shown for samples obtained four and eight weeks after each course of IL-2, as well as those obtained five or six days after (arrows) beginning each five-day course of IL-2. Levels of p24 antigen levels were determined by an immune complex dissociated assay (Coulter Corporation, Hialeah, Fla.) and particle-associated HIV RNA levels were determined on frozen samples using the bDNA signal amplification assay (Chiron Corporation, Emeryville, Calif.). Dewar et al., *J. Infec. Dis.* (1995); C. A. Pachl et al., Abstract 1247, 32nd INTERSCIENCE CONFERENCE ON ANTIMICROBIAL AGENTS AND CHEMOTHERAPY, October 1992; M. S. Urdea et al., NUCLEIC ACID RESEARCH SYMPOSIUM, Series 24, Oxford University Press, pages 1927–200 (1991).

Briefly, virus was concentrated from plasma using a bench top microcentrifuge (Heraeus Contifuge Model 17RS, rotor 3753; 23,500×g, 1 hour). The resultant virus pellet was lysed with 220 µl of a proteinase K/lithium lauryl sulfate buffer containing target probes complementary to pol gene sequences and then transferred to microwells of a 96-well plate. The RNA target was captured onto the microwell surface via specific capture probes during an overnight incubation at 53° C. The wells were washed and successively hybridized with the branched DNA amplifier (30 minutes), then alkaline phosphatase labeled probe (15 minutes). Finally, a chemiluminescent substrate, dioxetane, was added to each well and the enzyme-triggered light output was measured with a luminometer. The quantity of HIV RNA (reported as RNA equivalents/ml plasma) was calculated based on comparison to a standard curve. Signal was directly proportional to the amount of viral RNA present in the specimen. Not all samples were available at all time-points.

FIGS. 3F–3J shows that no significant changes were seen in p24 antigenemia during IL-2 therapy. FIGS. 3A–3E show that particle-associated plasma HIV RNA tended to increase transiently immediately after IL-2 therapy (arrows), then returned to baseline. All patients were receiving zidovudine throughout the study. In patient 3, the addition of didanosine at week 38 was associated with a substantial and sustained decrease in plasma particle-associated RNA levels.

No consistent changes in overall viral load in the peripheral blood, as evaluated by serial measurement of p24 antigen levels (FIGS. 3F–3J) or plasma viremia (data not shown), were detected during multiple-course IL-2 therapy. One patient showed a gradual decline, and two a gradual increase, in p24 antigen levels during a year of therapy. The other five patients remained consistently negative for p24 antigenemia.

Figure 3A:
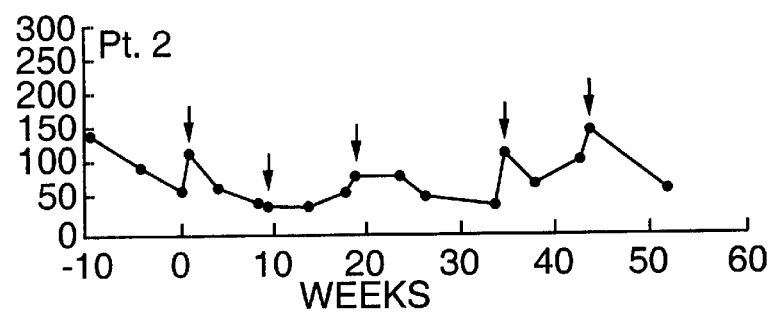
FIGS. 3A–3J show changes in retroviral markers during IL-2 therapy for patients 2, 3, 4, 6 and 8.
Figure 3B:
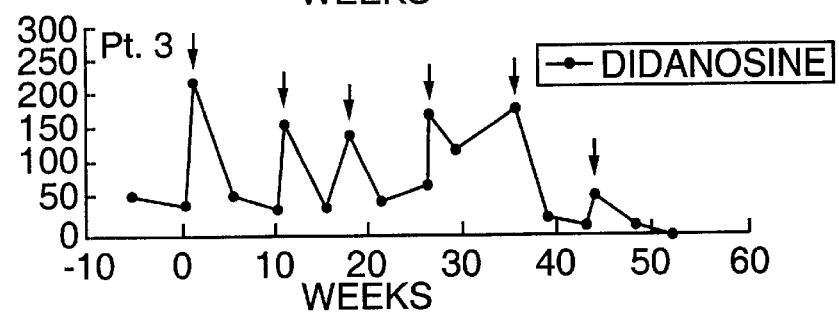
Figure 3C:
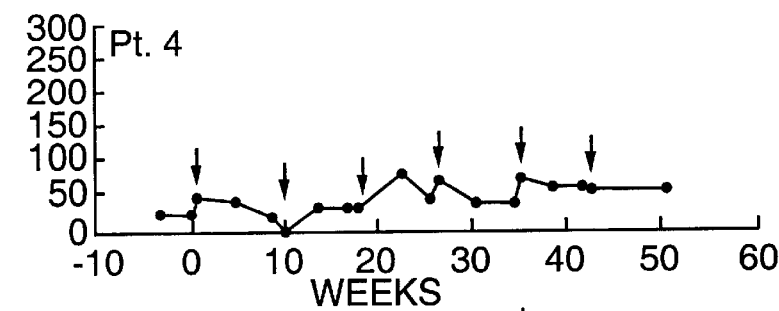
Figure 3D:
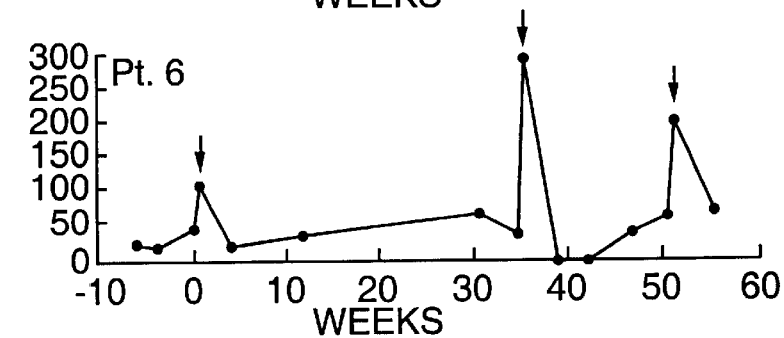
Figure 3E:
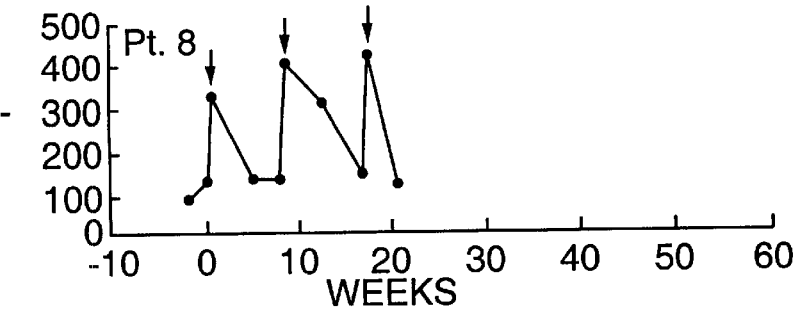
Figure 3F:
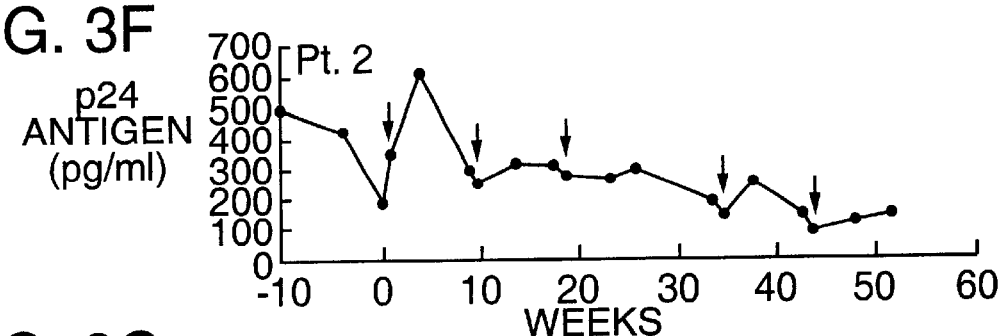
Figure 3G:
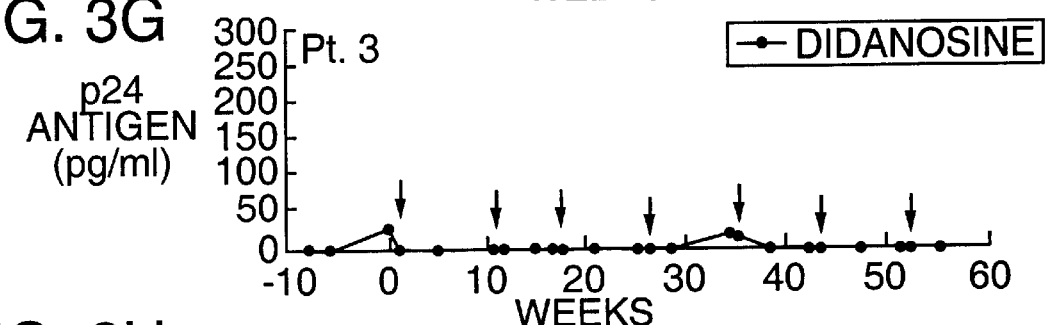
Figure 3H:
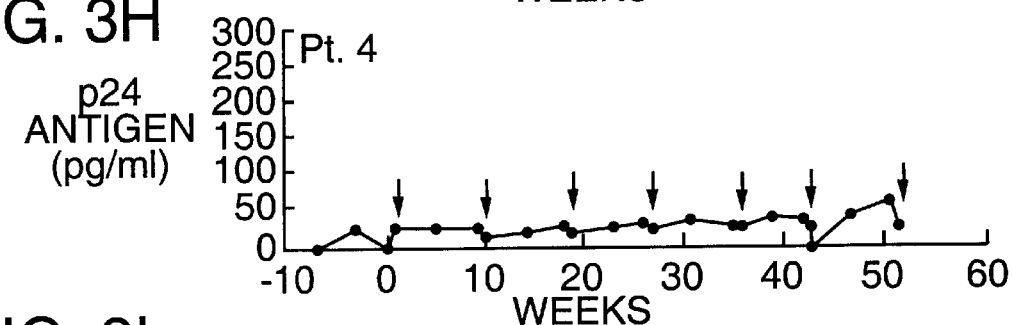
Figure 3I:
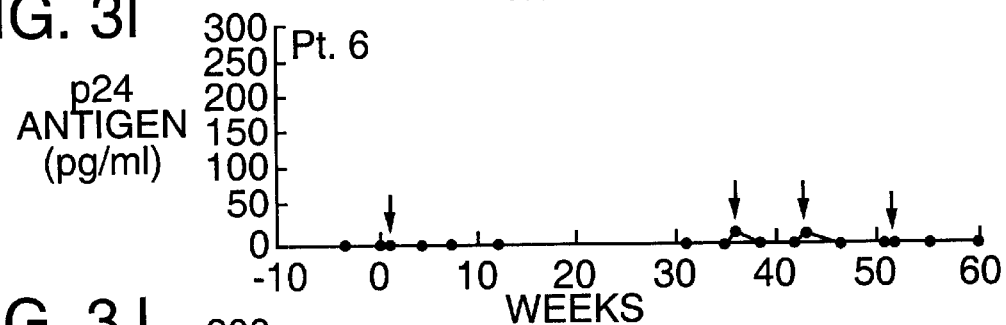
Figure 3J:
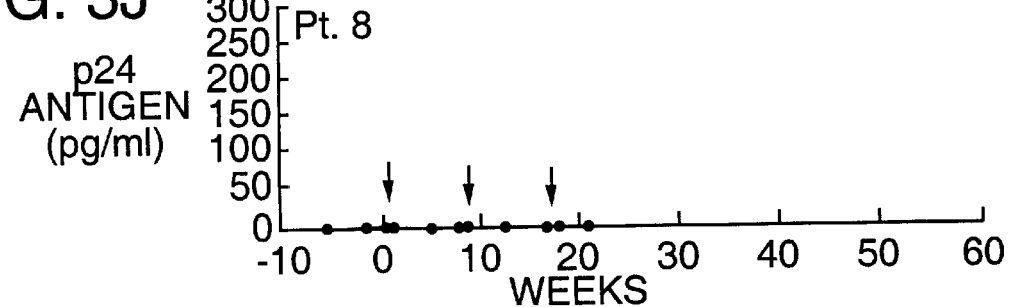

Because p24 antigen levels do not appear sensitive to acute changes in plasma viral burden, we assayed frozen plasma from six patients using a recently developed branched DNA assay that quantitatively measures HIV RNA (FIG. 3B). See Dewar et al., supra; Pachl et al., supra; M. S. Urdea et al., supra. In most patients, a consistent increase in particle-associated HIV RNA was noted immediately at the end of a course of IL-2; this increase was not associated with an increase in p24 antigen levels, and was almost always transient, with a return to baseline at the one- and two-month follow-up visits. The clinical significance of this transient burst in viral RNA is uncertain at present, but it likely represents replication of HIV following activation of lymphocytes. Alternatively, it could represent a redistribution of virus from lymph nodes or other sites to the blood. G. Pantaleo et al., *Nature* 36: 365–71 (1993).

In summary, six patients showed a sustained increase in CD4 number and/or percent following IL-2 therapy, with one patient increasing from 458 cells/mm$^3$ to 2130 cells/mm$^3$ during the first year of therapy. In addition to increased numbers of CD4 cells, measurements of CD4 function also showed improvement. Four of five initially unresponsive patients developed blastogenic responses to pokeweed mitogen, and two of seven initially unresponsive patients developed responses to tetanus toxoid. Thus, IL-2 therapy according to the present invention resulted in a decline in the percentage of lymphocytes expressing HLA-DR, and in an increase in the percentage of CD4 lymphocytes positive for the p55 IL-2 receptor. While no changes in HIV load were detected by p24 antigen and plasma viremia assays, a transient but consistent increase in plasma HIV RNA was detected by a new, sensitive branched DNA assay at the end of each infusion.

The patients had three to seven courses of IL-2, and follow-up ranged from 26 to 60 weeks. No patient developed an AIDS-defining opportunistic infection while on study. Accordingly, the use of IL-2 pursuant to the present invention reversed serious immunological abnormalities which are characteristic of HIV infection, especially CD4 cell depletion.

Figure 6:
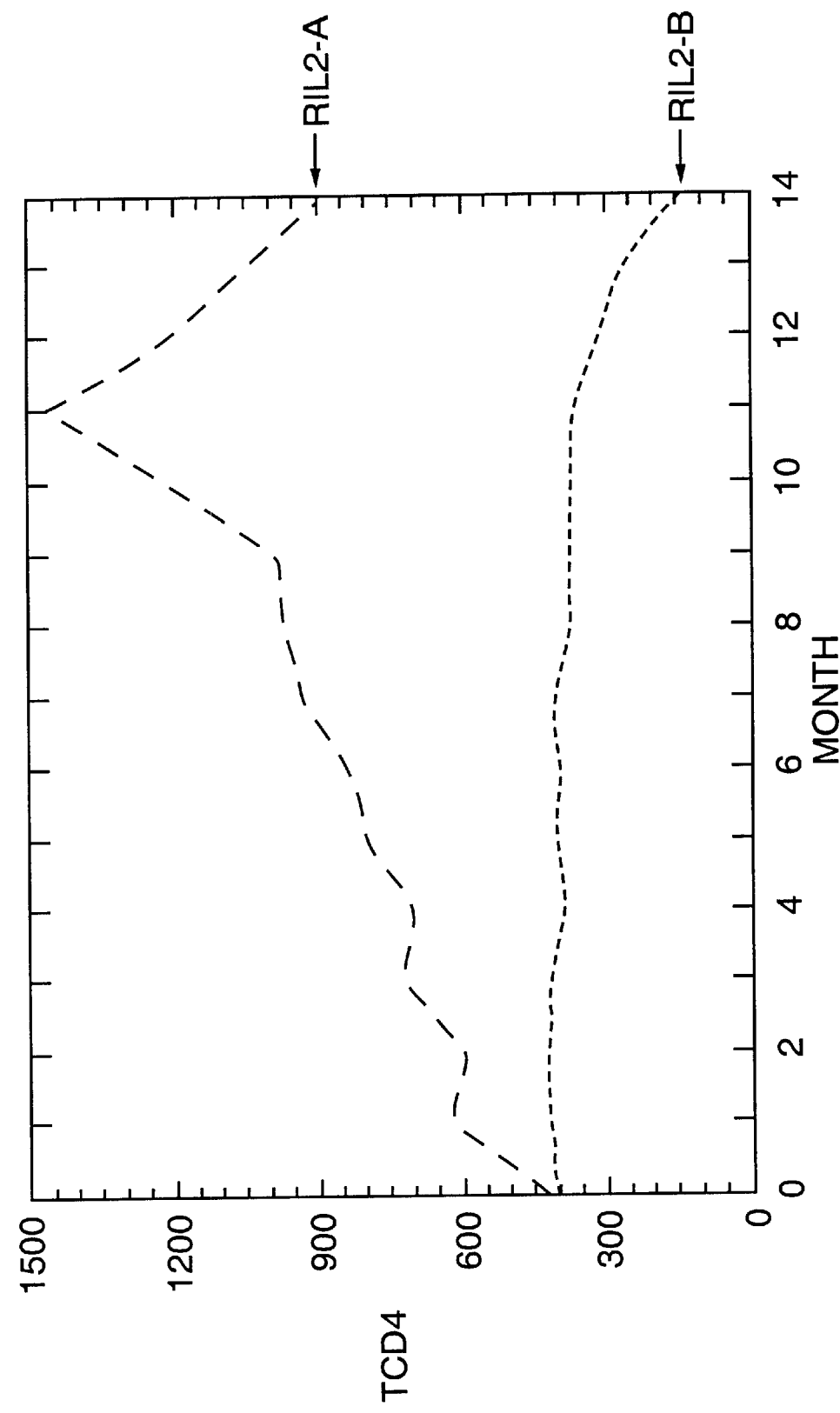
FIG. 6 shows changes in total CD4 (TCD4) count for patients receiving anti-retroviral therapy alone (Group B) or anti-retroviral therapy and intermittent IL-2 therapy (Group A).
Figure 7A:
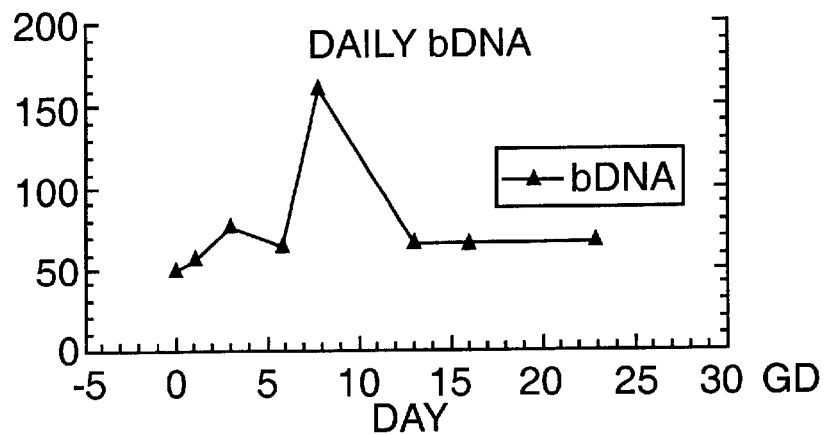
FIGS. 7A–7E show the daily bDNA (branched DNA) levels of patients undergoing intermittent IL-2 therapy.
Figure 7B:
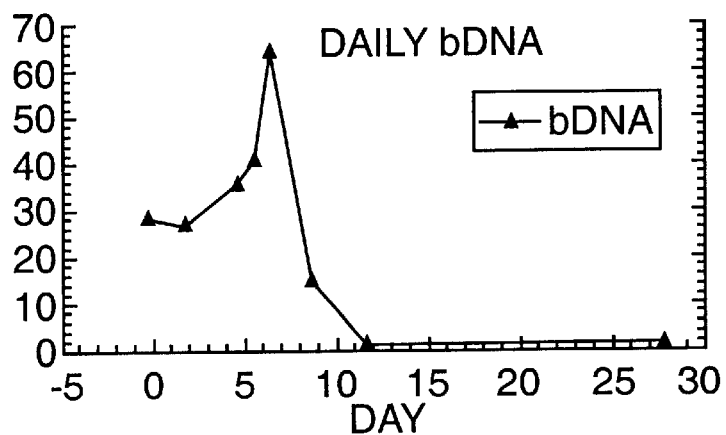
Figure 7C:
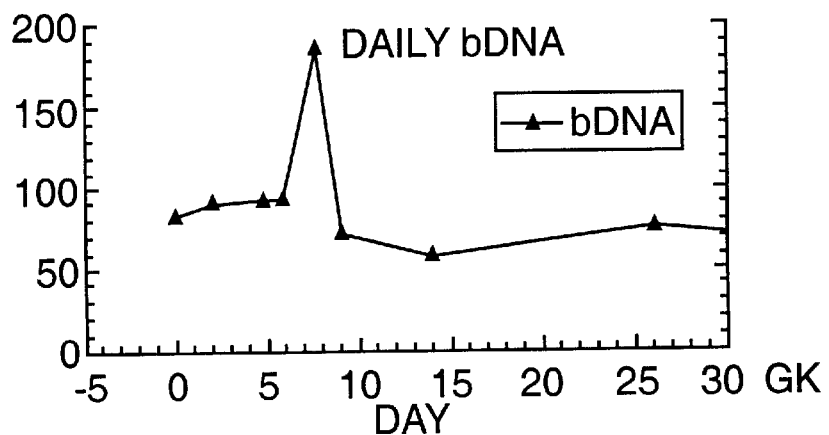
Figure 7D:
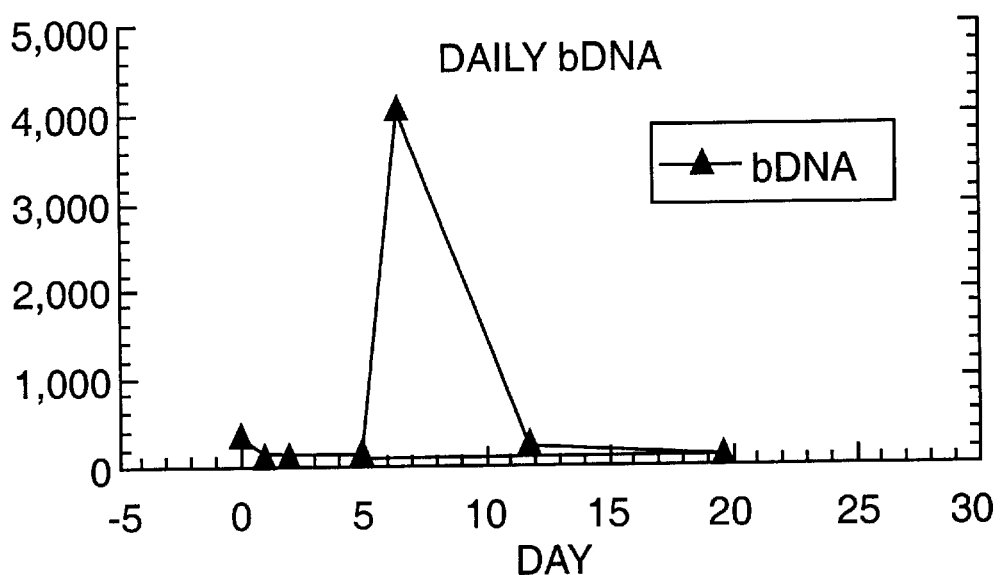
Figure 7E:
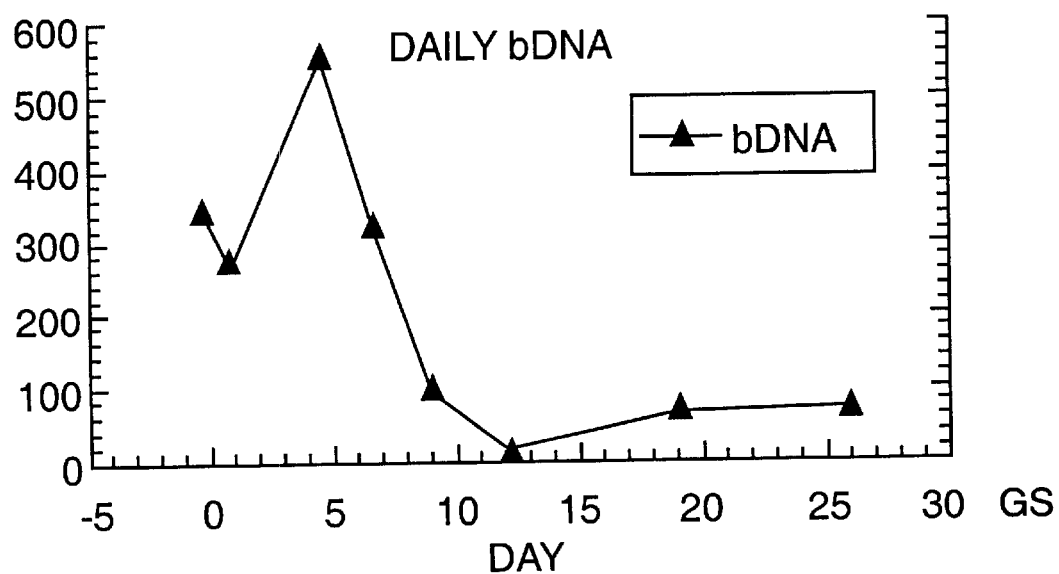

Ongoing studies demonstrate that intermittent IL-2 therapy enhances the immune system. The objective of one study is to examine the effects of intermittent IL-2 therapy in patients with HIV infection. At the beginning of the study, 31 patients were selected for administration of anti-retroviral therapy with intermittent IL-2 therapy (Group A) and 29 patients were selected for administration of anti-retroviral therapy alone (Group B). In this study, patients receive IL-2 as a continuous infusion approximately every eight weeks. Doses of IL-2 range from 6 to 18 MU over 24 hours for three to five days. FIGS. 5 and 6 show data obtained from the continuing study.

FIGS. 5 and 6 show the changes in CD4 and TCD4 (total CD4) counts for group A (receiving IL-2) and group B (not receiving IL-2). Table 3 contains the CD4 count data corresponding to FIGS. 5 and 6 for groups A and B, as well as the data for changes in the virologic parameters p24 and bDNA.

TABLE 3

Changes in CD4 and TCD4 (total CD4) counts and p24 and bDNA levels for group A (receiving IL-2) and group B (not receiving IL-2).

| # of Patients | Month | CD4 | TCD4 | P24 | BDNA |
|---|---|---|---|---|---|
| GROUP A | | | | | |
| 30 | 0 | 26 | 425 | 47 | 40 |
| 30 | 1 | 29 | 628 | 65 | 35 |
| 30 | 2 | 30 | 598 | 118 | 63 |
| 30 | 3 | 34 | 731 | 80 | 48 |
| 30 | 4 | 33 | 703 | 79 | 53 |
| 29 | 5 | 36 | 808 | 70 | 88 |
| 30 | 6 | 36 | 838 | 74 | 79 |
| 24 | 7 | 38 | 946 | 40 | 35 |
| 22 | 8 | 38 | 981 | 45 | 40 |
| 21 | 9 | 40 | 991 | 37 | 47 |
| 13 | 10 | 43 | 1214 | 53 | 44 |
| 10 | 11 | 48 | 1476 | 73 | 42 |
| 10 | 12 | 44 | 1219 | 65 | 38 |
| 6 | 13 | 45 | 1063 | 50 | 77 |
| 4 | 14 | 45 | 891 | 49 | 9 |
| GROUP B | | | | | |
| 29 | 0 | 26 | 406 | 60 | 41 |
| 29 | 1 | 26 | 420 | 69 | 47 |

TABLE 3-continued

Changes in CD4 and TCD4 (total CD4) counts and p24 and bDNA levels for group A (receiving IL-2) and group B (not receiving IL-2).

| # of Patients | Month | CD4 | TCD4 | P24 | BDNA |
|---|---|---|---|---|---|
| 29 | 2 | 25 | 423 | 72 | 38 |
| 29 | 3 | 26 | 415 | 84 | 58 |
| 29 | 4 | 25 | 382 | 72 | 50 |
| 29 | 5 | 24 | 403 | 82 | 56 |
| 28 | 6 | 25 | 395 | 64 | 90 |
| 26 | 7 | 25 | 413 | 96 | 100 |
| 24 | 8 | 24 | 372 | 66 | 96 |
| 20 | 9 | 24 | 377 | 56 | 254 |
| 18 | 10 | 22 | 370 | 52 | 150 |
| 15 | 11 | 21 | 368 | 78 | 159 |
| 10 | 12 | 17 | 316 | 95 | 144 |
| 8 | 13 | 15 | 270 | 184 | 246 |
| 4 | 14 | 13 | 151 | 20 | 87 |

Based on a statistical analysis of the individual patients, the TCD4 curves of FIG. 6 are likely different with a probability of 95% (p=0.05) and the CD4 curves are likely different with a probability of 96% (p=0.04). Table 4 is a standard 2-sided, non-paired t-test comparison of the groups through the first six months of treatment. This analysis illustrates the statistical significance of the results.

TABLE 4

Standard Non-paired Two Sided T-test

| Month | p value (CD4 percent) | p value (CD4 count) |
|---|---|---|
| 0 | .74 | .79 |
| 1 | .19 | .002 |
| 2 | .10 | .007 |
| 3 | .006 | <.001 |
| 4 | .006 | <.001 |
| 5 | .001 | .001 |
| 6 | .003 | .001 |

Table 5 illustrates the increases in both memory and naive T cells during the treatment with IL-2. The data in this table illustrate that both memory and naive T-cell levels are increased by the intermittent IL-2 therapy.

TABLE 5

Increases In Both Memory And Naive Cells Occur During Treatment With Intermittent Continuous Infusions of IL-2

| Patient/Time | Total CD4 Count | Total Memory CD4 T Cells* | Total Naive CD4 T Cells+ |
|---|---|---|---|
| 1/Month 0 | 643 | 443 | 200 |
| 1/Month 1 | 885 | 550 | 335 |
| 1/Month 2 | 900 | 669 | 230 |
| 2/Month 0 | 590 | 512 | 79 |
| 2/Month 1 | 848 | 636 | 212 |
| 2/Month 2 | 991 | 764 | 227 |
| 3/Month 0 | 476 | 386 | 90 |
| 3/Month 1 | 1288 | 868 | 420 |
| 3/Month 2 | 1263 | 1156 | 107 |

Figure 16:
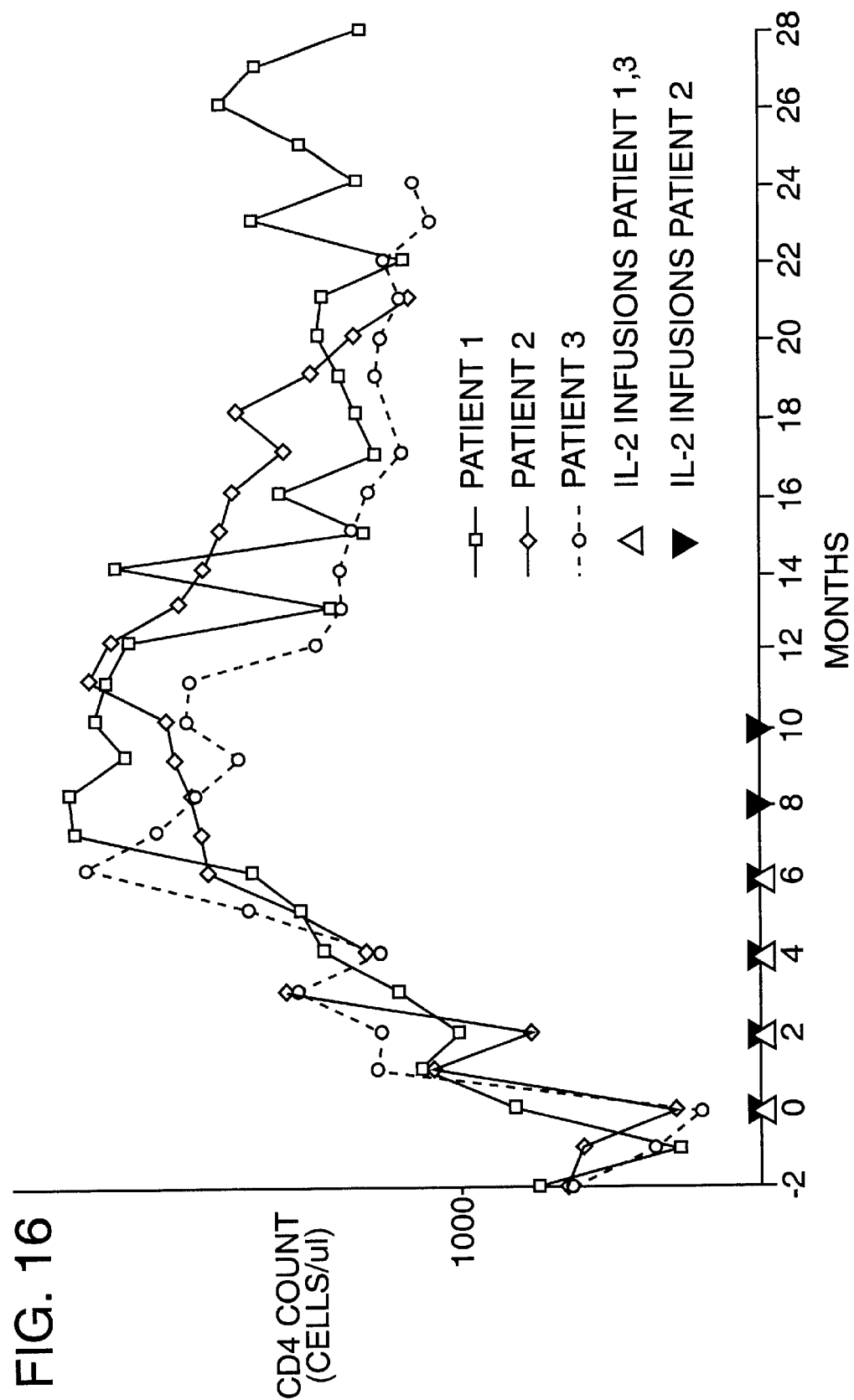
FIG. 16 shows the persistent elevations in CD4 count of three patients who received intermittent continuous infusions of IL-2 over 6–10 months.
Figure 17:
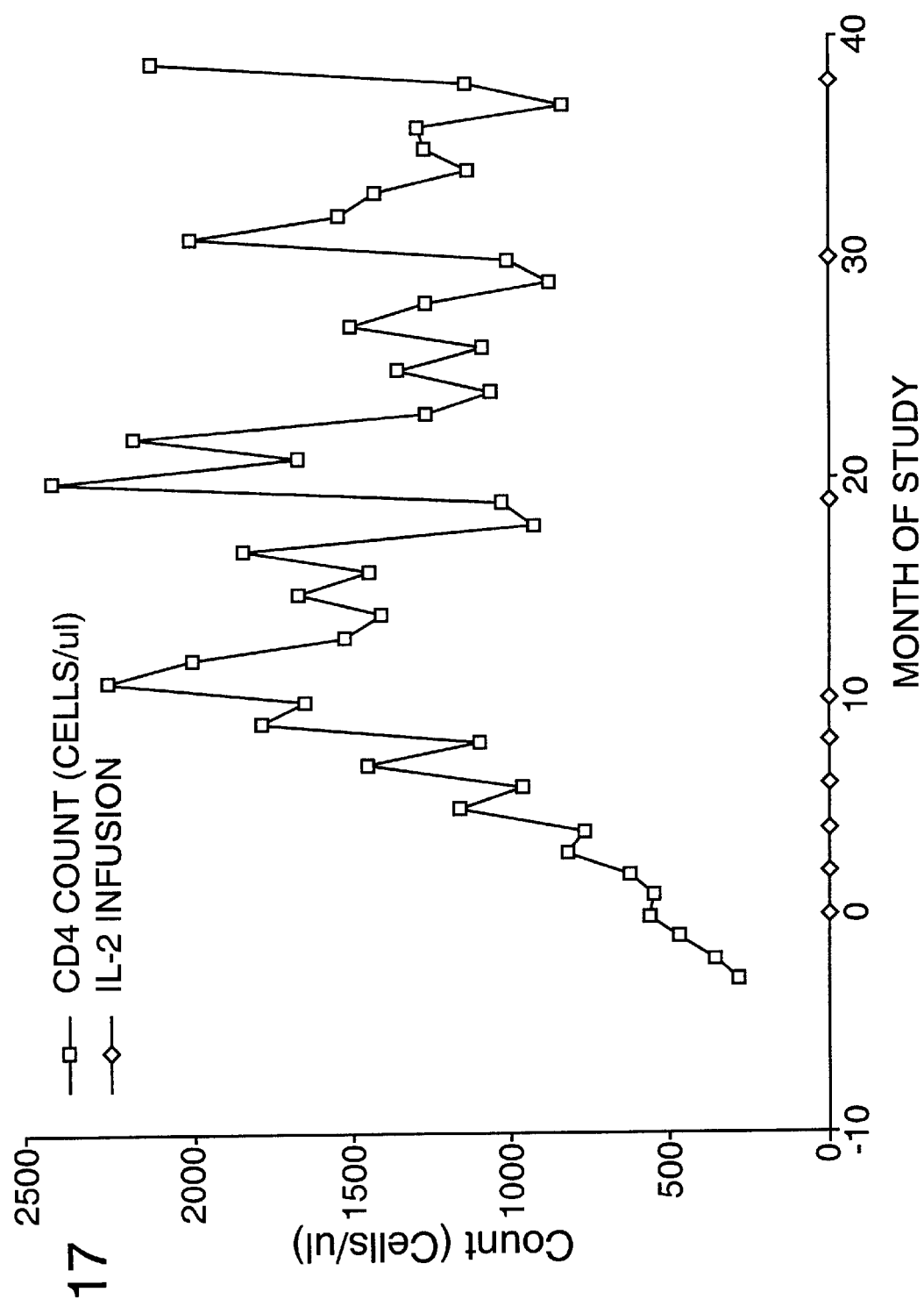
FIG. 17 shows the elevations in CD4 count of a patient receiving intermittent continuous infusions of IL-2 over 3 years.
Figure 18:
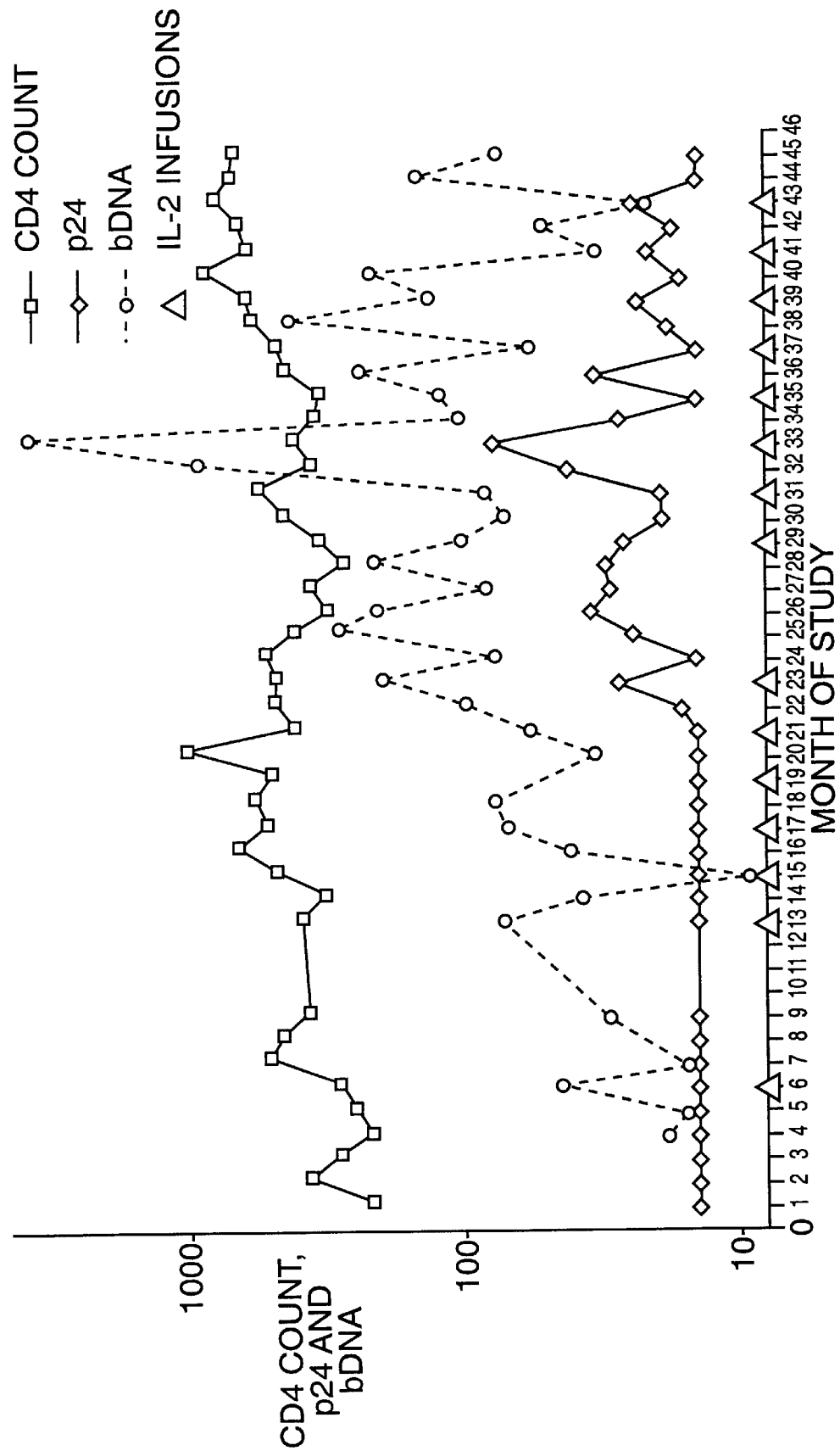
FIG. 18 shows changes in CD4 count, bDNA and p24 of a patient receiving intermittent continuous infusions of IL-2 over 4 years.
Figure 20:
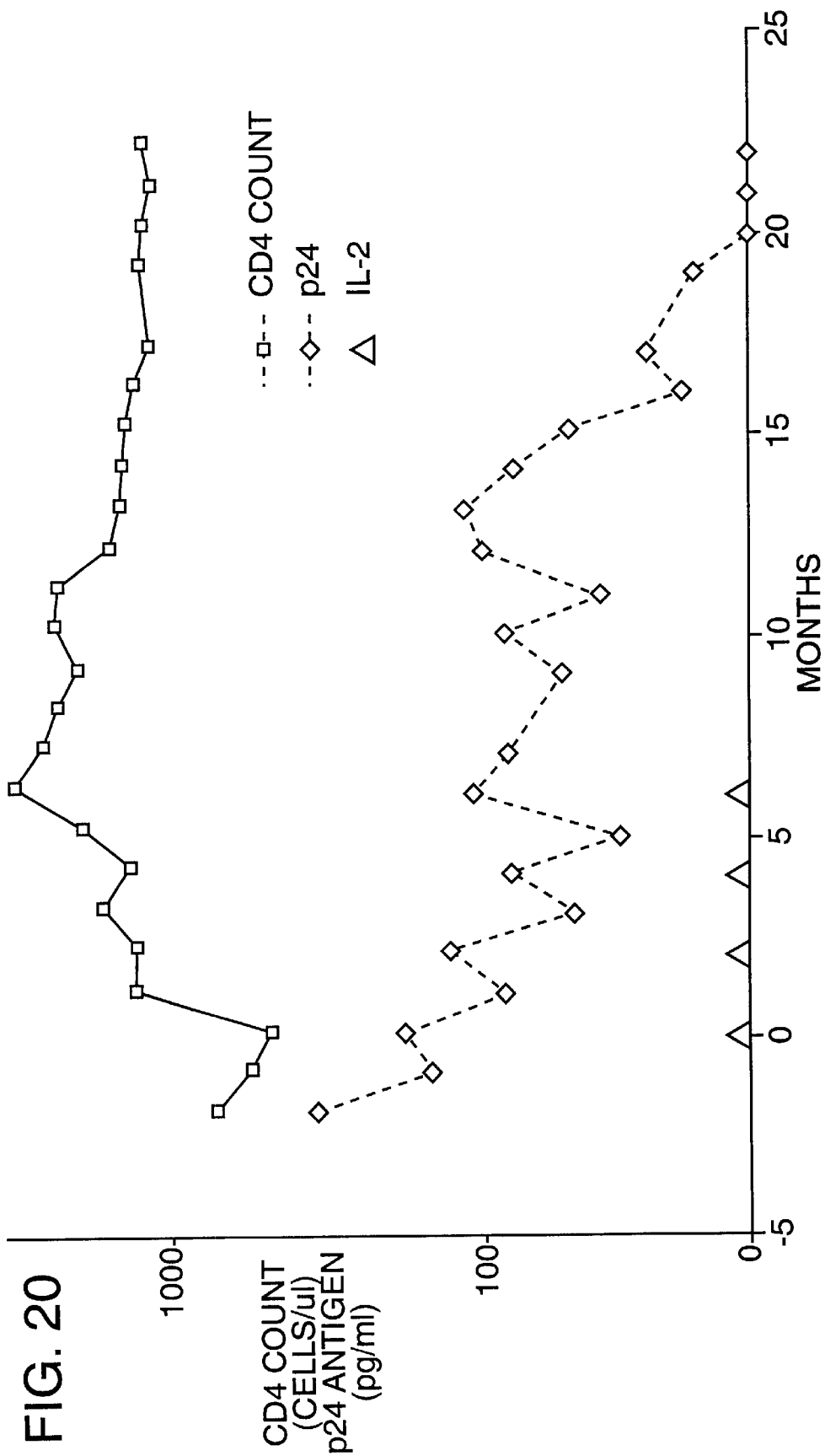
FIG. 20 shows the persistent decline in p24 antigen levels in a patient undergoing 22 months of intermittent IL-2 therapy. This figure also shows the change in CD4 count observed in this patient.

*Defined by the presence of the CD45Ro+ phenotype
+Defined by the presence of the CD45Ro− phenotype FIG. 16 shows the elevations in CD4 count of three patients receiving intermittent continuous infusions of IL-2 over 6–10 months. FIG. 17 shows the elevations in CD4 count of a patient receiving intermittent continuous infusions of IL-2 over 3 years. FIG. 18 shows changes in CD4 count, bDNA and p24 of a patient receiving intermittent continuous infusions of IL-2 over 4 years. FIG. 20 shows the persistent decline in p24 antigen levels in a patient undergoing 22 months of intermittent IL-2 therapy. This Figure also shows the change in CD4 count observed in this patient.

A cohort of 27 patients with CD4 counts over 200 have received IL-2 as a continuous infusion approximately every eight weeks in addition to anti-retroviral therapy. Doses of IL-2 ranged from 6 to 18 MU over 24 hours for three to five days. After six months of IL-2 treatment, 19 patients (70%) had a 25% or greater increase in CD4 count, 16 patients (59%) had a 50% or greater increase in CD4 count, and 9 patients (33%) had a 100% or greater increase in CD4 count.

Accordingly, the clinical studies evidence the efficacy of IL-2 therapy in the amplification of immune function.

EXAMPLE 4

Combined IL-2/Gene Therapy

Interleukin-2 would be given as a continuous infusion at a dose of 6–18 MU/day for a period of six days. At day 5 of the IL-2 infusion the patient would be administered intravenously with a replication-defective, amphotropic retrovirus or with plasmid DNA containing a gene that will confer a new property to the cells, such as rendering cells resistant to HIV infection. Due to the state of activation of the cells (FIG. 4), the genetic information of the retrovirus or the plasmid is incorporated into the genetic information of the cell, rendering that cell resistant to HIV infection.

This method also could be used to broaden the antigen-specific repertoire of the immune system by using recombinant retroviruses or plasmids that contain genetic information for specific antigen receptors.

EXAMPLE 5

Intermittent IL-2 Therapy with Subcutaneous Administrations of IL-2

Figure 9:
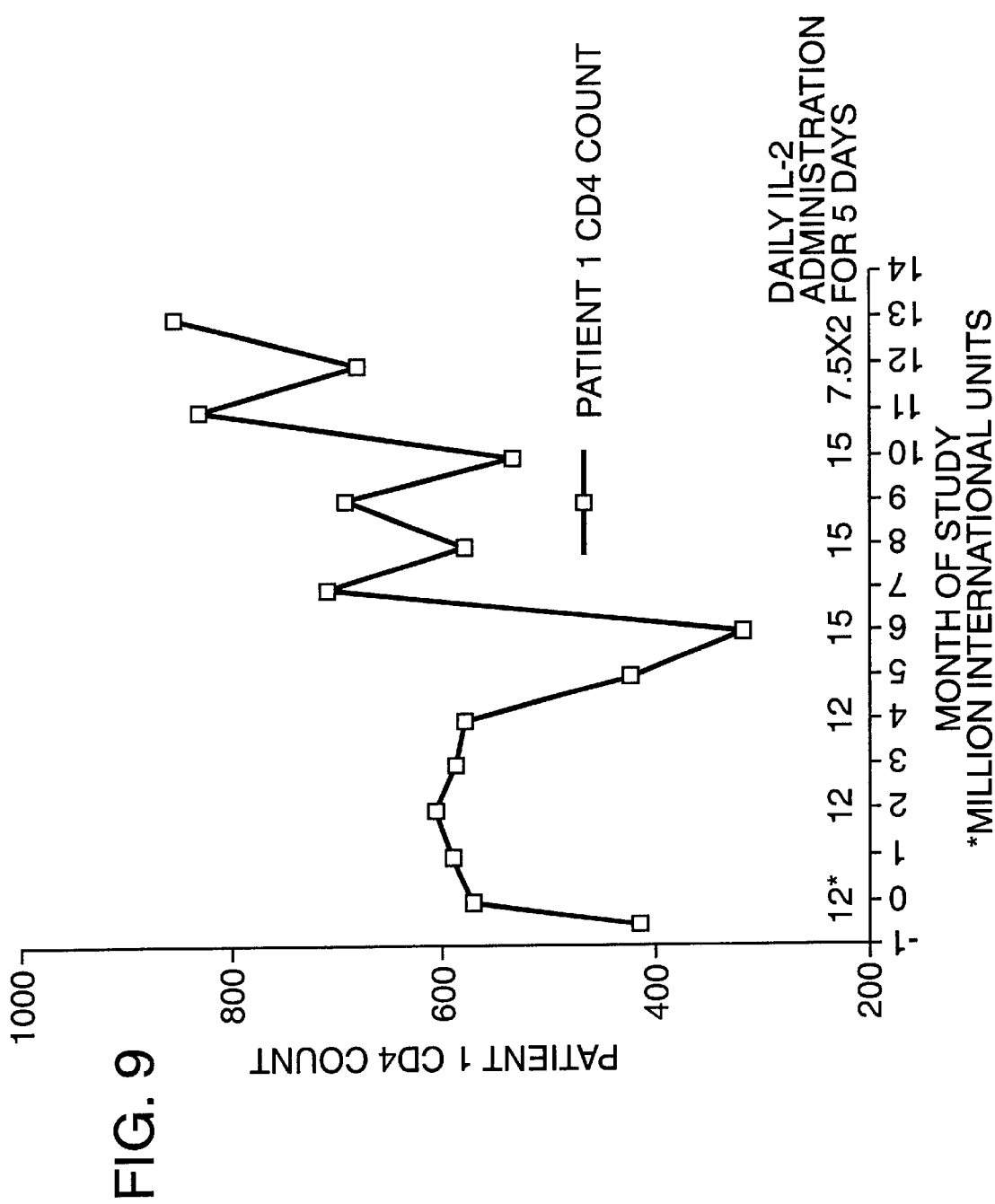
FIGS. 9, 10 and 11 show increases in CD4 counts in patients receiving intermittent IL-2 therapy according to the present invention, with the IL-2 administered by subcutaneous injection.
Figure 10:
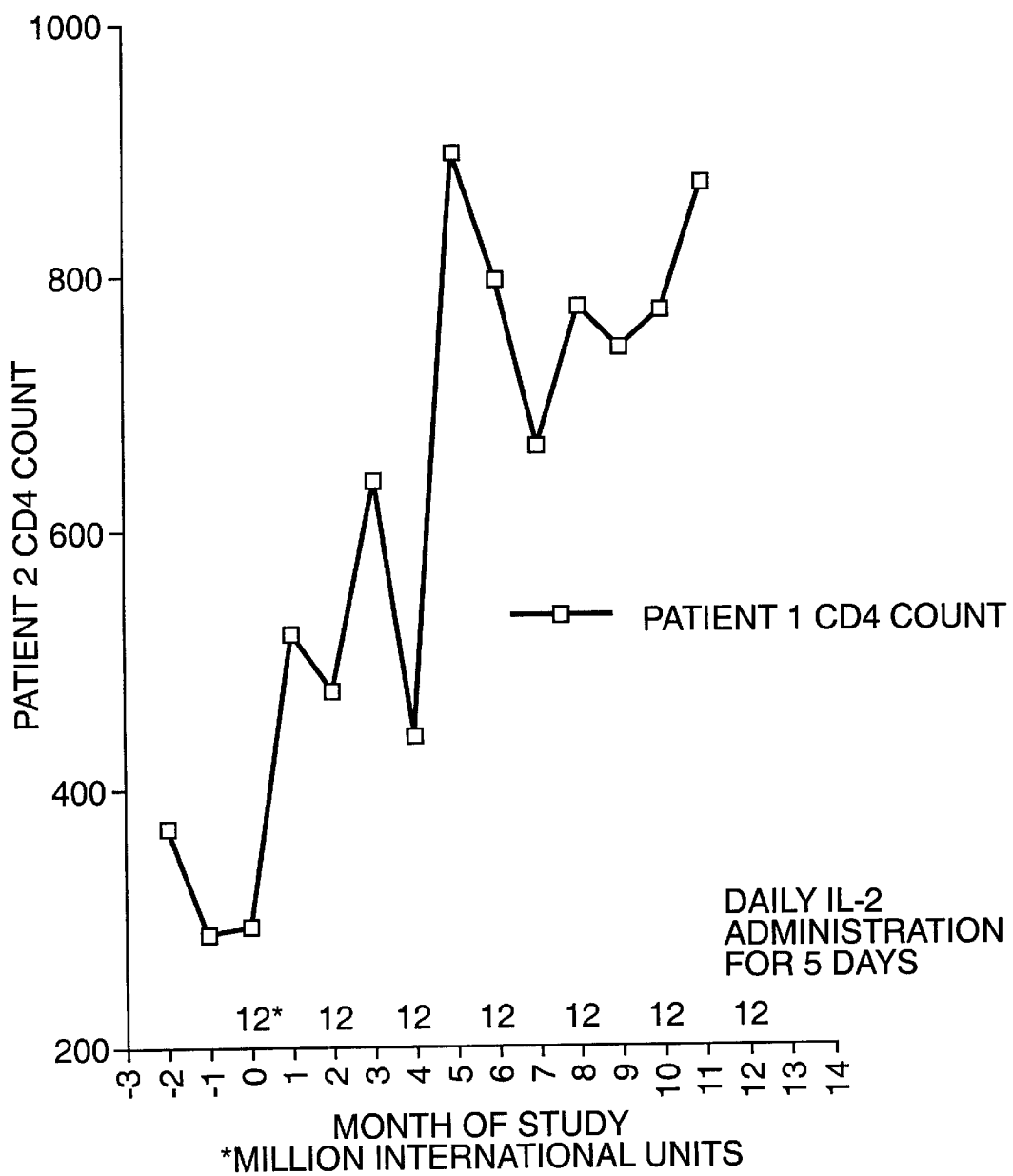
Figure 11:
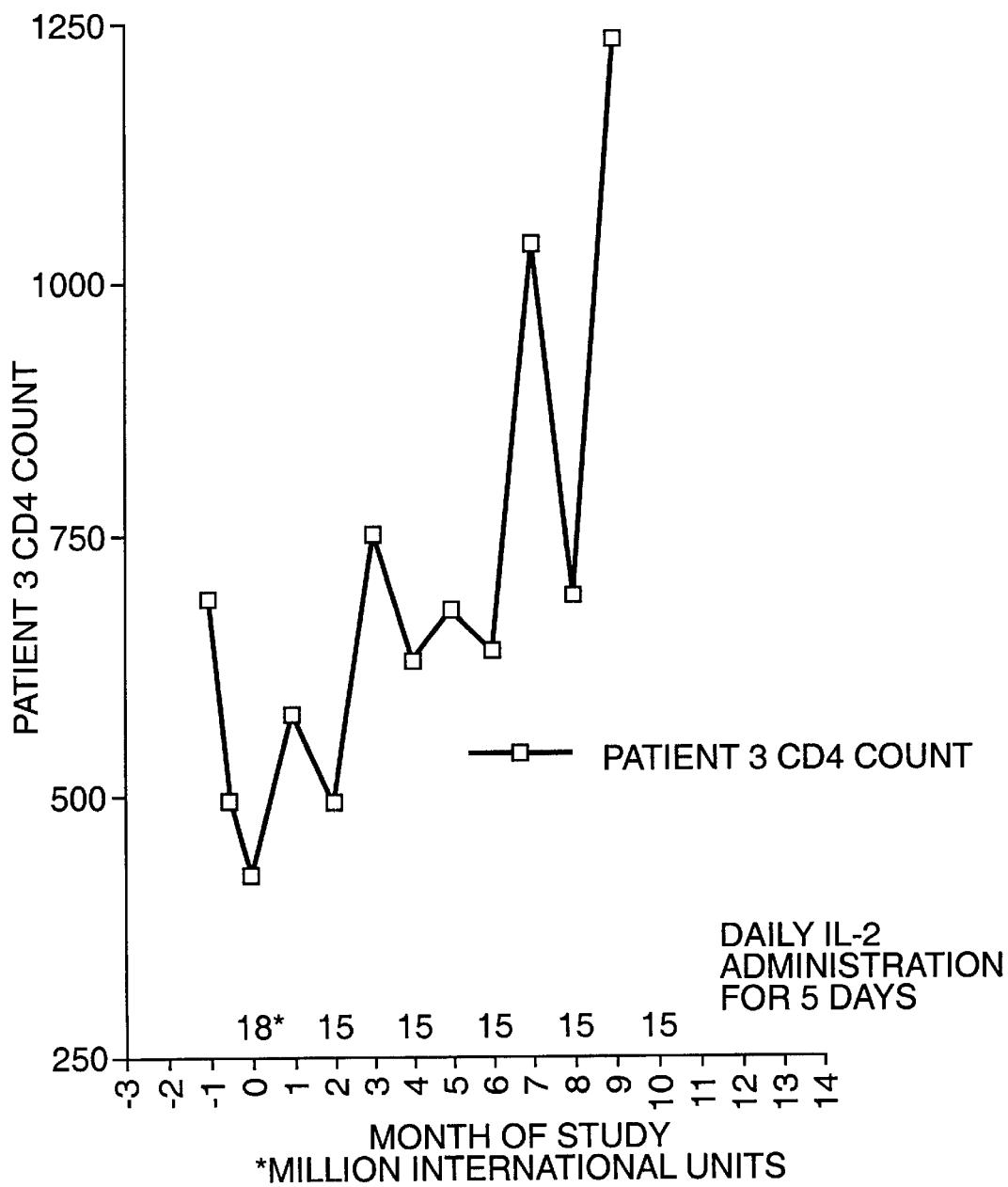

The efficacy of subcutaneous IL-2 was evaluated using the same surrogate endpoints evaluated in the continuous infusion trials discussed above. The maximum tolerated dose of subcutaneous IL-2 delivered as a five day outpatient regimen was found to be comparable to the maximum tolerated dose of IL-2 administered by subcutaneous infusion. Patients were given IL-2 at doses of 12–18 MU/day for 5 days every two months. FIGS. 9, 10 and 11 show the results of patients followed for up to 1 year. At the last reported administration, Patient 1 received a divided dose of IL-2 of 7.5 MU two times per day. The data in these figures show that the beneficial effects of the intermittent IL-2 therapy of the present invention can be achieved with subcutaneous administrations of IL-2.

EXAMPLE 6

Intermittent IL-2 Therapy of a Non-HIV Infected Patient

Figure 8:
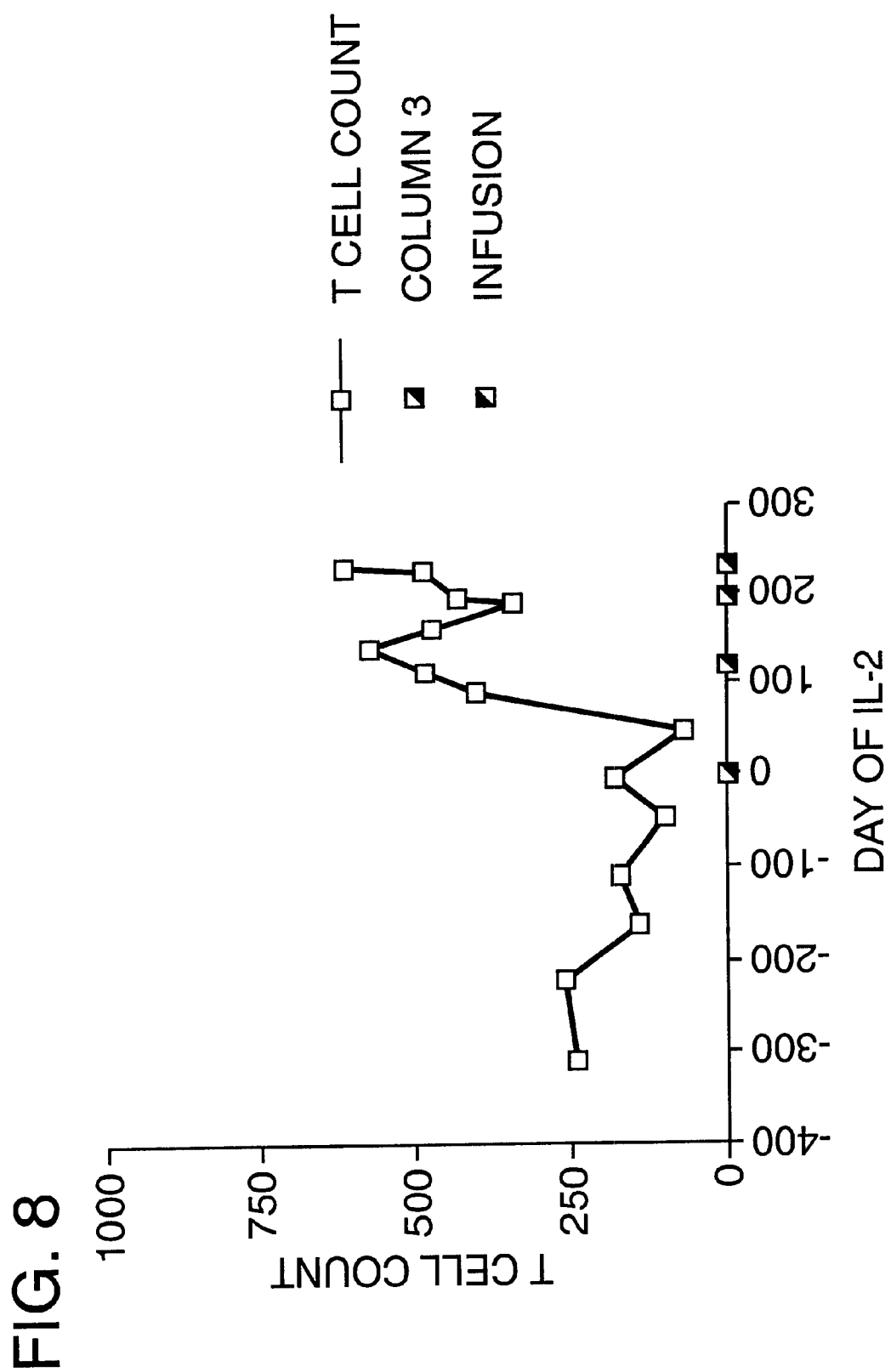
FIG. 8 shows changes in total lymphocyte count for a non-HIV-infected patient with idiopathic CD4 lymphopenia who received intermittent IL-2 therapy in addition to therapy with antibiotics and gamma interferon.

FIG. 8 shows the change in total lymphocyte count for a non-HIV-infected patient receiving intermittent IL-2 therapy. The patient was a woman with an unexplained defect in T-cell function, manifest by disseminated mycobacterium avium-intracellular infection and an Epstein-Barr virus associated lymphoma. She was undergoing treatment with antibiotics and gamma interferon. At each time point indicated on the graph, she received a continuous infusion course of IL-2 at a dosage of 6–18 MU/day for up to 5 days. When infusions were as close as one month apart, she demonstrated a marked increase in T cell count. Unfortunately, this intervention was not adequate to reverse the-course of her cancer, and she died. However, it is important to note that at autopsy there was no evidence of the mycobacterial infection. This patient illustrates the ability of the intermittent IL-2 therapy described in the above-identified application to treat a disease state other than HIV infection.

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A method for treating a subject having an HIV infection, comprising
    administering to the subject in a series of administrations an amount of IL-2 sufficient to increase the CD4 count in the patient as compared with the count prior to IL-2 administration, wherein the administration of IL-2 is continuous over a period of time that is sufficient to allow spontaneous DNA synthesis in peripheral blood or lymph node cells of the subject to increase and peak;
    administering to the subject an anti-retroviral agent to lower the HIV viral burden.

2. The method of claim 1, wherein each of said series of administrations is continuous over a period of time of time from 1 day to 2 weeks, and wherein successive infusions are separated by a period of time of about 4 weeks.

3. The method of claim 1, wherein the anti-retroviral agent comprises U-90152, PMEA, a protease inhibitor, a zinc finger inhibitor, interferon alpha, amantadine, rimantadine, arildone, ribaviran, acyclovir, 9-[1,3-dihydroxy-2-propoxy)methyl]guanine (DHPG), vidarabine (ARA-A), ganciclovir, enviroxime, foscarnet, interferon alpha, interferon beta, and interferon gamma, ampligen, podophyllotoxin, 2,3-dideoxycytidine (DDC), idodeoxyuridine (IDU), triflorothymidine (TFT), dideoxyinosine (ddi), d4T, 3TC, zidovudine, a specific antiviral immune globulin, or a combination thereof.

4. The method of claim 1, wherein the anti-retroviral agent comprises zidovudine.

5. The method of claim 1, further comprising administering a retroviral vector encoding a T cell receptor.

6. The method of claim 1, wherein the IL-2 is administered at a dosage from 1.0 to 2.4 million international units per day (MU/day).

7. A method of activating cells of the immune system, comprising
    administering IL-2 to the cells in a series of administrations effected intermittently, each of the administrations is continuous over a period of time from 1 day to 2 weeks, wherein the administrations are separated by a period of time of at least four weeks;
    wherein the administering of IL-2 results in increasing spontaneous DNA synthesis in the cells, and enhancing the susceptibility of the cells to transformation with a vector as compared to untreated cells, thereby activating the cells of the immune system.

8. The method of claim 7, wherein the IL-2 is administered at a dosage from 1.0 to 2.4 million international units per day (MU/day).

9. The method of claim 7, wherein each administration is about 3 to about 5 days in length.

10. The method of claim 7, wherein the vector is a viral vector.

11. The method of claim 10, wherein the viral vector is a retroviral vector.

* * * * *